(12) United States Patent
Assens et al.

(10) Patent No.: US 6,949,583 B2
(45) Date of Patent: Sep. 27, 2005

(54) AMINOALKOXYBENZOYL-BENZOFURAN OR BENZOTHIOPHENE DERIVATIVES, METHOD OF PREPARING SAME AND COMPOSITIONS CONTAINING SAME

(75) Inventors: Jean-Louis Assens, Grabels (FR); Claude Bernhart, Saint Gely du Fesc (FR); Frédérique Cabanel-Haudricourt, Pignan (FR); Patrick Gautier, Cournonterral (FR); Dino Nisato, Saint Georges d'Orques (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/362,324

(22) PCT Filed: Aug. 21, 2001

(86) PCT No.: PCT/FR01/02640

§ 371 (c)(1),
(2), (4) Date: Feb. 20, 2003

(87) PCT Pub. No.: WO02/16339

PCT Pub. Date: Feb. 28, 2002

(65) Prior Publication Data

US 2003/0225100 A1 Dec. 4, 2003

(30) Foreign Application Priority Data

Aug. 23, 2000 (FR) .......................................... 00 10834

(51) Int. Cl.⁷ .................... A61K 31/343; C07D 307/78; C07D 307/87

(52) U.S. Cl. ....................... 514/469; 549/429; 549/462; 549/468; 514/449; 514/461

(58) Field of Search .................................. 549/429, 462, 549/468, 434, 436; 514/461, 469, 448, 464, 465

(56) References Cited

U.S. PATENT DOCUMENTS

| | | | |
|---|---|---|---|
| 3,248,401 A | | 4/1966 | Tondeur et al. |
| 4,806,663 A | | 2/1989 | Kennedy et al. |
| 4,851,554 A | * | 7/1989 | Kennedy et al. ............ 549/471 |
| 5,100,911 A | | 3/1992 | Binder et al. |
| 5,223,510 A | * | 6/1993 | Gubin et al. ................ 514/299 |

FOREIGN PATENT DOCUMENTS

| | | |
|---|---|---|
| EP | 0617030 | 9/1994 |
| EP | 0835871 | 4/1998 |
| WO | WO 90/02743 | 3/1990 |
| WO | WO 94/29289 | 12/1994 |
| WO | WO 95/10513 | 4/1995 |

\* cited by examiner

*Primary Examiner*—Golam M M Shameem
(74) *Attorney, Agent, or Firm*—Jiang Lin

(57) ABSTRACT

The invention relates to benzofuran or benzothiophene derivatives, to processes for preparing them, to pharmaceutical compositions comprising them, and to the method of use thereof in the treatment of pathological syndromes of the cardiovascular system.

23 Claims, No Drawings

AMINOALKOXYBENZOYL-BENZOFURAN OR BENZOTHIOPHENE DERIVATIVES, METHOD OF PREPARING SAME AND COMPOSITIONS CONTAINING SAME

The present invention relates, generally, to novel heterocyclic derivatives and to their process of preparation.

The invention thus relates to novel benzofuran or benzothiophene derivatives of general formula:

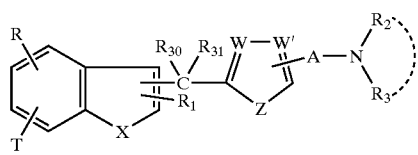

(1)

and to their pharmaceutically acceptable salts, in which formula:

A represents a linear or branched $C_1$–$C_5$ alkylene group optionally substituted by a hydroxyl group or A represents a group of general formula:

$$—R_{19}—O—R_{20}—$$ (h)

in which $R_{19}$ and $R_{20}$, which are identical or different, each represent a linear or branched $C_1$–$C_4$ alkylene group, $R_{30}$ and $R_{31}$, taken together, represent a carbonyl group with the carbon to which they are attached or represent a group of general formula:

$$—O—R_{29}—O—$$ (m)

in which $R_{29}$ represents a $C_1$–$C_4$ alkylene group,

T represents hydrogen or a $C_1$–$C_4$ alkyl radical,

R represents:
the cyano, hydroxymethyl, formyl or tetrazolyl group,
an ester group of general formula:

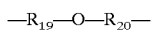

(a)

in which $R_4$ represents a linear or branched $C_1$–$C_6$ alkyl group or a $C_3$–$C_6$ cycloalkyl group, a carboxyl group of general formula:

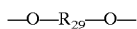

(b)

in which $R_5$ represents hydrogen or an alkali metal atom, an amide group of general formula:

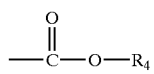

(c)

in which $R_6$ and $R_7$, which are identical or different, represent hydrogen or a linear or branched $C_1$–$C_4$ alkyl radical or $R_6$ and $R_7$, when they are taken together, represent a $C_2$–$C_6$ alkylene chain, a ketone group of general formula:

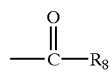

(d)

in which $R_8$ represents a $C_1$–$C_4$ alkyl group, an oxime group of general formula:

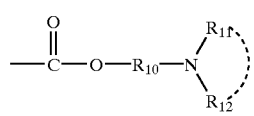

(f)

in which $R_9$ represents hydrogen or a $C_1$–$C_4$ alkyl radical, a carboxyl group of general formula:
in which $R_{10}$ represents a linear or branched $C_1$–$C_4$ alkylene group, $R_{11}$ represents hydrogen or a $C_1$–$C_4$ alkyl radical, $R_{12}$ represents a $C_1$–$C_4$ alkyl radical or $R_{11}$ and $R_{12}$, when they are taken together, represent a $C_2$–$C_6$ alkylene chain, a group of general formula:

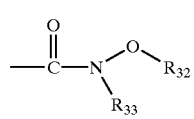

(g)

in which $R_{32}$ and $R_{33}$, which are identical or different, represent a linear or branched $C_1$–$C_4$ alkyl group, $R_1$ represents hydrogen, a linear or branched $C_1$–$C_6$ alkyl group, a $C_3$–$C_6$ cycloalkyl group, a benzyl group or a phenyl group optionally substituted by one or more substituents selected from halogen atoms, $C_1$–$C_4$ alkyl groups or $C_1$–$C_4$ alkoxy groups or $R_1$ represents a group of general formula:

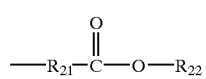

(i)

in which $R_{21}$ represents a linear or branched $C_1$–$C_4$ alkylene group and $R_{22}$ represents a linear or branched $C_1$–$C_4$ alkyl group or $R_1$ represents a group of general formula:

$$—R_{23}—OH$$ (j)

in which $R_{23}$ represents a linear or branched $C_1$–$C_6$ alkylene group, $R_2$ and $R_3$, which are identical or different, represent hydrogen, a linear or branched $C_1$–$C_6$ alkyl group optionally substituted by one or more, preferably from 1 to 4, halogen atoms or by a pyrrolidinyl group, a $C_3$–$C_6$ cycloalkyl group or a group of general formula:

$$—R_{24}—O—R_{25}$$ (k)

in which $R_{24}$ represents a linear or branched $C_1$–$C_4$ alkylene group and $R_{25}$ represents a linear or branched $C_1$–$C_4$ alkyl group, or $R_2$ and $R_3$, when they are taken together, represent a linear or branched $C_3$–$C_{10}$ alkylene group or represent, with the nitrogen atom to which they are attached, a group of general formula:

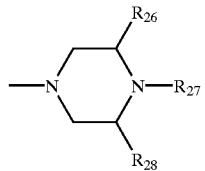
(I)

in which:

R$_{26}$, R$_{27}$ and R$_{28}$, which are identical or different, represent hydrogen or a linear or branched C$_1$–C$_4$ alkyl group, or R$_{26}$ represents hydrogen or a linear or branched C$_1$–C$_4$ alkyl group and R$_{27}$ and R$_{28}$, when they are taken together, represent a linear or branched C$_1$–C$_4$ alkylene group, these alternatives, R$_2$ and R$_3$, which are identical or different, and R$_2$ and R$_3$, taken together, being represented in the formula (1) by the symbol

situated between R$_2$ and R$_3$

W, W' and Z are such that:
when W and W', which are identical, represent CH, Z represents —O— or —S—,
when W represents CH and W' represents C—R$_{13}$, Z represents

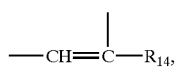

R$_{13}$ and R$_{14}$ being identical or different and representing hydrogen, a halogen atom, a C$_1$–C$_4$ alkyl radical or a C$_1$–C$_4$ alkoxy radical, X represents —O— or —S—, these benzofuran or benzothiophene derivatives being in the form of individual isomers or of mixtures of the latter.

In particular, the benzofuran or benzothiophene derivatives according to the invention are characterized in that A represents a linear or branched C$_1$–C$_5$ alkylene group.

More particularly, the benzofuran or benzothiophene derivatives according to the invention are characterized in that R$_1$ represents hydrogen, a linear or branched C$_1$–C$_6$ alkyl group, a C$_3$–C$_6$ cycloalkyl group, a benzyl group or a phenyl group optionally substituted by one or more substituents selected from halogen atoms, C$_1$–C$_4$ alkyl groups or C$_1$–C$_4$ alkoxy groups.

More specifically, the invention relates to novel benzofuran or benzothiophene derivatives which can be represented by the general formula:

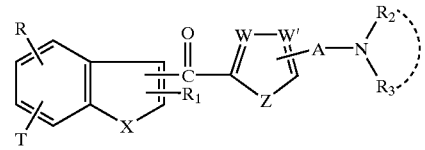
(1-1)

in which:

A represents a linear or branched C$_1$–C$_5$ alkylene group,

T represents hydrogen or a C$_1$–C$_4$ alkyl radical,

R represents:
the cyano, hydroxymethyl, formyl or tetrazolyl group,
an ester group of general formula:

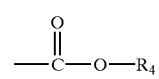
(a)

in which R$_4$ represents a C$_1$–C$_6$ alkyl or C$_3$–C$_6$ cycloalkyl group, a carboxyl group of general formula:

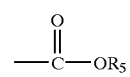
(b)

in which R$_5$ represents hydrogen or an alkali metal atom, an amide group of general formula:

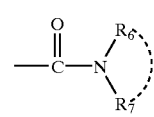
(c)

in which R$_6$ and R$_7$, which are identical or different, represent hydrogen or a linear or branched C$_1$–C$_4$ alkyl radical or R$_6$ and R$_7$, when they are taken together, represent a C$_2$–C$_6$ alkylene chain, a ketone group of general formula:

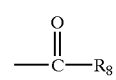
(d)

in which R$_8$ represents a C$_1$–C$_4$ alkyl group, an oxime group of general formula:

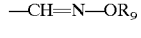
(e)

—CH=N—OR$_9$ in which R$_9$ represents hydrogen or a C$_1$–C$_4$ alkyl radical, a carboxyl group of general formula:

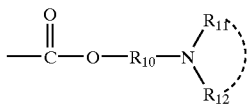 (f)

in which $R_{10}$ represents a linear or branched $C_1$–$C_4$ alkylene group, $R_{11}$ represents hydrogen or a $C_1$–$C_4$ alkyl radical and $R_{12}$ represents a $C_1$–$C_4$ alkyl radical or $R_{11}$, and $R_{12}$, when they are taken together, represent a $C_2$–$C_6$ alkylene chain, $R_1$ represents hydrogen, a linear or branched $C_1$–$C_6$ alkyl group, a $C_3$–$C_6$ cycloalkyl group, a benzyl group or a phenyl group optionally substituted by one or more substituents selected from halogen atoms, $C_1$–$C_4$ alkyl groups or $C_1$–$C_4$ alkoxy groups, $R_2$ and $R_3$, which are identical or different, represent hydrogen, a linear or branched $C_1$–$C_6$ alkyl group or a $C_3$–$C_6$ cycloalkyl group, or $R_2$ and $R_3$, when they are taken together, represent a linear or branched $C_3$–$C_{10}$ alkylene group, these alternatives, $R_2$ and $R_3$, which are identical or different, and $R_2$ and $R_3$, taken together, being represented in the formula (1—1) by the symbol

situated between $R_2$ and $R_3$

W, W' and Z are such that:
  when W and W', which are identical, represent CH, Z represents —O— or —S—,
  when W represents CH and W' represents C—$R_{13}$, Z represents

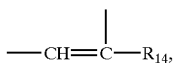

$R_{14}$, $R_{13}$ and $R_{14}$ being identical or different and representing hydrogen, a halogen atom, for example chlorine or bromine, a $C_1$–$C_4$ alkyl radical, such as methyl, or a $C_1$–$C_4$ alkoxy radical, such as methoxy, X represents —O— or —S—.

Classes of preferred compounds of the invention can be represented by the compounds of formula (1):
  in which R represents an isopropoxycarbonyl group
  or in which $R_1$ and/or $R_2$ and/or $R_3$ represent the n-butyl group
  or in which X represents —O—.

Another class of preferred compounds of formula (1) is that in which

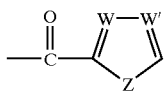

represents the benzoyl radical.

Likewise, a specific class of compounds of formula (1) is that in which the entity:

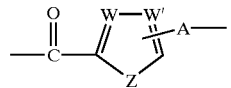

represents a benzoyl radical substituted in the 4-position by an -A- group.

Finally, the compounds of formula (1) in which $R_1$ represents n-butyl, A represents the propylene group and $R_2$ and $R_3$, which are identical, represent the n-butyl group can be regarded as preferred.

Compounds of formula (1) can exist in the form of optical or geometrical isomers, for example the compounds in question in which $R_2$ and $R_3$, taken with the nitrogen atom to which they are attached, represent a diethylpiperidino group or in which R represents a group (e).

Consequently, the invention relates both to the individual isomers of the compounds of formula (1) and to their mixtures, in particular the racemic mixture.

The invention also relates to the pharmaceutically acceptable salts of the compounds of formula (1) formed from an organic or inorganic acid.

Mention may be made, as examples of organic salts of this type, of the oxalate, maleate, fumarate, methanesulphonate, benzoate, ascorbate, pamoate, succinate, hexamate, bismethylenesalicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate, p-toluenesulphonate and theophyllineacetate salts and the salts formed from an amino acid, such as the lysine or histidine salt.

Mention may be made, as inorganic salts of this type, of the hydrochloride, hydrobromide, sulphate, sulphamate, phosphate and nitrate salts.

It has been found that the compounds of the invention possess noteworthy pharmacological properties, in particular antiarrhythmic properties, since they have proved to be capable of suppressing or preventing disorders of the ventricular and auricular rhythm. Most of the compounds of the invention have electrophysiological properties of classes 1, 2, 3 and 4 of the Vaughan-Williams classification, which confer bradycardic, antihypertensive and anti-α-adrenergic and anti-β-adrenergic properties which are noncompetitive. Furthermore, the majority of the compounds have also displayed antioxidizing properties, an affinity for sigma receptors and an ability to enhance the synthesis of NO.

Furthermore, these compounds of the invention demonstrate inhibitory properties with respect to various hormonal agents, such as, for example, angiotensin II, arginine vasopressin, neuropeptide Y or endothelin.

These properties are capable of rendering the compounds in question very useful in the treatment of certain pathological syndromes of the cardiovascular system, in particular in the treatment of angina pectoris, hypertension, arrhythmia, in particular atrial, ventricular or supraventricular arrhythmia, or cerebral circulatory insufficiency. Likewise, the compounds of the invention can be used in the treatment of cardiac insufficiency or myocardial infarction, complicated or not complicated by cardiac insufficiency, or for the prevention of post-infarction mortality.

In the antitumour field, the compounds of the invention may be of use as potentiators of antineoplastics.

Consequently, the invention also relates to a medicament, characterized in that it comprises a compound derived from benzofuran or benzothiophene, or a pharmaceutically acceptable salt of the latter, according to the invention.

Consequently, the invention also relates to pharmaceutical or veterinary compositions comprising, as active principle, at least one compound of the invention in combination with an appropriate excipient or pharmaceutical vehicle.
Depending upon the administration route chosen, the daily dosage for a human being weighing 60 kg will lie between 2 and 2000 mg of active principle, in particular between 50 and 500 mg of active principle.
The compounds of formula (1) can be prepared according to the following methods:

A.—In the case where R represents the cyano group, the formyl group, a group (a), a group (d), a group (e) or a group (f), by reacting a compound of general formula:

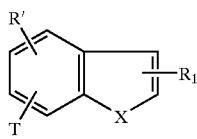

(2)

in which R' represents the cyano group, the formyl group, a group (a), a group (d), a group (e) or a group (f) and $R_1$, T and X have the same meaning as above, with a halide of general formula:

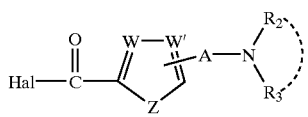

(3)

in which A, $R_2$, $R_3$, W, W' and Z have the same meaning as above and Hal represents a halogen atom, such as, for example, chlorine or bromine, the reaction taking place in the presence of a Lewis acid, such as aluminium chloride, stannic chloride, ferric chloride or silver trifluoromethanesulphonate, which gives the desired compounds of formula (1) in the free base form.

Usually, the above reaction takes place in a nonpolar solvent, such as a halogenated compound, for example dichloromethane or dichloroethane, and at a temperature of between 5° C. and the reflux temperature.

B.—In the case where R represents a group (b), by saponifying, in the presence of a basic agent, namely an alkali metal hydroxide, for example sodium hydroxide, a compound of above formula (1) in which R represents a group (a), that is to say a compound of general formula:

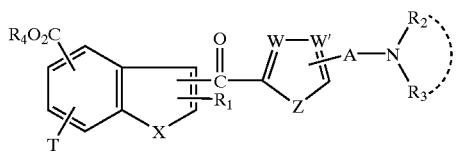

(4)

in which A, $R_1$, $R_2$, $R_3$, $R_4$, T, W, W', X and Z have the same meaning as above, which gives, in the free base form, the compounds of formula (1) in which $R_5$ represents an alkali metal atom, which compounds are treated, if necessary, with a strong acid, for example hydrochloric acid, which gives, in the free base form, the desired compounds of formula (1) in which $R_5$ represents hydrogen.

C.—In the case where R represents the hydroxymethyl group, by deprotecting a ketal of general formula:

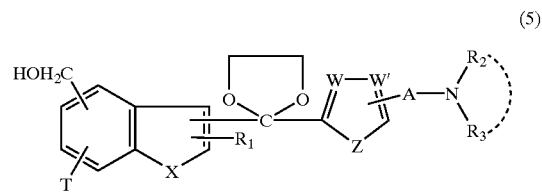

(5)

in which A, $R_1$, $R_2$, $R_3$, T, X, W, W' and Z have the same meaning as above, by means of pyridine p-toluenesulphonate and preferably at the reflux temperature, which gives the desired compounds of formula (1) in the free base form.

Alternatively, compounds of formula (1) can be obtained by employing the following processes:

D.—In the case where R represents the cyano group, the formyl group, a group (a), a group (d), a group (e) or a group (f) and $R_2$ and $R_3$, which are identical, each represent hydrogen, by treating, with triphenylphosphine, an azide of general formula:

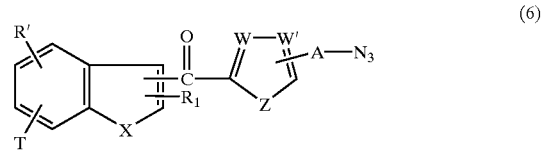

(6)

in which A, R', $R_1$, T, W, W', X and Z have the same meaning as above, to form the derived compounds of formula (1) in the free base form.

E.—In the case where R represents the cyano group, the formyl group, a group (a), a group (b), a group (e) or a group (f) and A represents a linear or branched $C_3$–$C_5$ alkylene group or a group (h), by reacting a ketone compound of general formula:

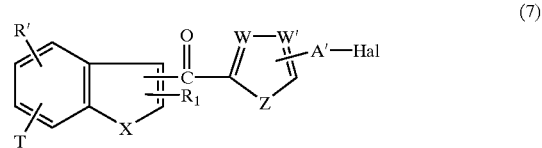

(7)

in which A' represents a linear or branched $C_3$–$C_5$ alkylene group and Hal, R', $R_1$, T, W, W', X and Z have the same meaning as above, with a compound of general formula:

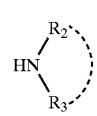

(8)

in which $R_2$ and $R_3$ have the same meaning as above, the reaction taking place in the presence of a basic agent, such as an alkali metal carbonate or hydroxide or an excess of compound of formula (8) in the basic form, which gives the desired compounds of formula (1) in the free base form.

Generally, the reaction takes place at a temperature between ambient temperature and the reflux temperature of the solvent and in a polar solvent, such as N,N-dimethylformamide, acetonitrile, methyl ethyl ketone or dimethyl sulphoxide, or a nonpolar solvent, such as benzene or toluene.

Furthermore, this reaction is usually carried out in the presence of a catalyst, preferably sodium iodide or potassium iodide.

Finally, in the alternative form where A represents a $C_3$–$C_5$ alkylene group substituted by a hydroxyl group, instead of the compound (7), a compound of general formula:

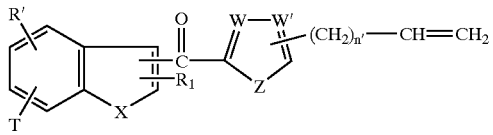

(67)

in which n' has the value 0 or is an integer between 1 and 3, is reacted with meta-chloroperbenzoic acid to produce the epoxide of general formula:

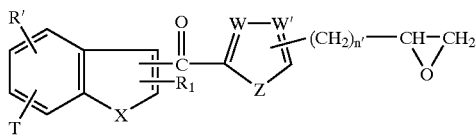

(68)

which is subsequently reacted with an amine of formula (8) as described above for the compound (7). The compound of formula:

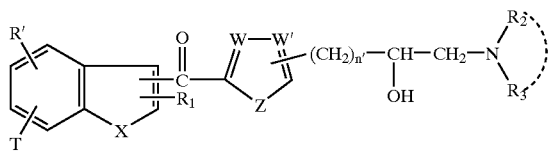

(69)

is thus obtained.

F.—In the case where R represents the cyano group, the formyl group, a group (a), a group (d), a group (e) or a group (f), $R_2$ represents hydrogen or a linear or branched $C_1$–$C_6$ alkyl group and $R_3$ represents a linear or branched $C_1$–$C_6$ alkyl group, by reacting an amine of general formula:

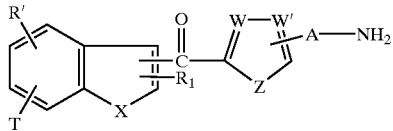

(9)

in which A, R', $R_1$, T, X, W, W' and Z have the same meaning as above, with an aldehyde of general formula:

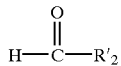

(10)

in which R'$_2$ represents hydrogen or a $C_1$–$C_5$ alkyl radical, in the presence of sodium triacetoxyborohydride, to give the desired compounds of formula (1) in the free base form.

The benzofuran or benzothiophene derivatives of formula (1) which also correspond to the general formula:

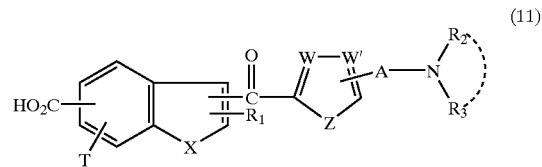

(11)

in which A, $R_1$, $R_2$, $R_3$, T, W, W', X and Z have the same meaning as above, are themselves synthetic intermediates for the preparation of other compounds of formula (1).

To this end, the following methods, starting from the compounds of formula (11) in question, can be employed to obtain the desired compounds of formula (1), that is to say:

G.—In the case where R represents a group (c), by reacting a compound of formula (11), after protection of the amine functional group when $R_2$ and/or $R_3$ represent hydrogen, preferably in a halogenated hydrocarbon as solvent and generally at the reflux temperature, with a halogenating agent, such as thionyl chloride, phosgene or oxalyl chloride, to produce an acyl halide, which is subsequently treated, preferably at ambient temperature, with a compound of general formula:

(12)

in which $R_6$ and $R_7$ have the same meaning as above, and then, if necessary, the compound formed is deprotected, which gives the desired compounds of formula (1) in the free base form.

H.—In the case where R represents a group (a), by reacting a compound of formula (11), after protection of the amine functional group when $R_2$ and/or $R_3$ represent hydrogen, preferably in a halogenated hydrocarbon as solvent and generally at the reflux temperature, with a halogenating agent, such as thionyl chloride, phosgene or oxalyl chloride, to produce an acyl halide, which is subsequently treated, preferably at a temperature between ambient temperature and the reflux temperature, with an alcohol of general formula:

$$R_4—OH \quad (13)$$

in which $R_4$ has the same meaning as above, and then, if necessary, the compound formed is deprotected, which gives the desired compounds of formula (1) in the free base form.

I.—In the case where R represents a group (f):
a) if this group (f) is of the primary dialkylaminoalkyl type, a compound of formula (11), after protection of the amine functional group when $R_2$ and/or $R_3$ represent hydrogen, is reacted, preferably in a polar solvent, such as N,N-dimethylformamide, and usually at a temperature of between 30 and 50° C., with an alcohol of general formula:

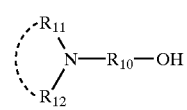

(14)

in which $R_{11}$ and $R_{12}$ have the same meaning as above and $R_{10}$ represents a linear $C_1$–$C_4$ alkylene group, the reaction taking place in the presence of carbonyldiimidazole and 1,8-diazabicyclo[5.4.0]-undec-7-ene, and then, if necessary, the compound formed is deprotected, which gives, in the free base form, the desired compounds of formula (1), b) if this group (f) is of the secondary or tertiary dialkylaminoalkyl type, a compound of formula (11), after protection of the amine functional group when $R_2$ and/or $R_3$ represent hydrogen, is reacted, preferably in an aprotic solvent, such as a halogenated hydrocarbon, and generally at the reflux temperature of the medium, with a halogenating agent, such as thionyl chloride, to produce an acyl halide, which is subsequently treated, preferably at ambient temperature, with an alcohol of above formula (14), in which $R_{11}$ and $R_{12}$ have the same meaning as above and $R_{10}$ represents a secondary or tertiary $C_2$–$C_4$ alkylene group, and then, if necessary, the compound formed is deprotected, which gives the compounds of formula (1) in the hydrohalide form or in the free base form, which hydrohalide can be treated, if necessary, with a basic agent, such as an alkali metal hydroxide or an alkali metal carbonate, to produce the desired compounds in the free base form.

In the above processes G, H and I, the protection of the amine functional group of the compound of formula (10), that is to say the protection envisaged when $R_2$ and/or $R_3$ represent hydrogen, can be obtained, for example, by treatment by means of a compound which makes possible the attachment of a group which can be easily removed, in particular by means of 9-fluorenylmethyl chloroformate, and the deprotection is subsequently carried out by treatment with a secondary amine, for example piperidine or diethylamine, in an appropriate solvent, for example N,N-dimethylformamide.

I-1. In the case where R represents a group (g), by reacting a compound of general formula

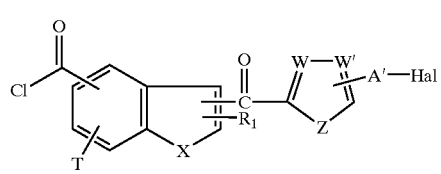

(64)

in which A', Hal, $R_1$, T, W, W', X and Z have the same meaning as above, with a compound of general formula:

 (65)

to obtain the compound of general formula:

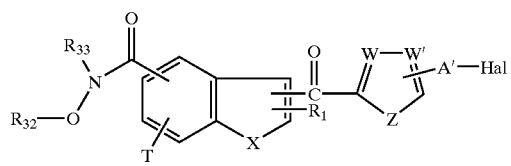

(66)

which is subsequently reacted with an amine of formula (8) as described above for the compound (7).

Other compounds of formula (1) can be used as synthetic intermediates for compounds of the invention, in particular the cyano derivatives which also correspond to the general formula:

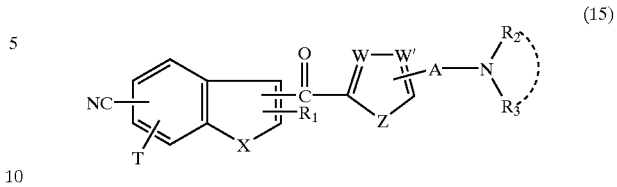

(15)

in which A, $R_1$, $R_2$, $R_3$, T, W, W', X and Z have the same meaning as above.

Thus, the following methods can be employed, that is to say:

J.—In the case where R represents a group (c) in which $R_6$ and $R_7$ each represent hydrogen, a compound of formula (15) is hydrolysed in the presence of a strong acid, such as, for example, sulphuric acid, and generally at ambient temperature, which gives, in the free base form, the desired compounds of formula (1).

K.—In the case where R represents the tetrazolyl group, a compound of formula (15) is reacted, preferably in an aprotic solvent, such as an aromatic hydrocarbon, for example benzene or toluene, and usually at the reflux temperature of the medium, with a tri($C_1$–$C_4$ alkyl)azidotin, for example tributylazidotin, which gives, in the free base form, the desired compounds of formula (1).

In another way, the compounds of formula (1) in which R represents the cyano group, the formyl group, a group (a), a group (d), a group (e) or a group (f) and in which $R_2$ and $R_3$, which are different, each represent a linear or branched $C_1$–$C_6$ alkyl group or a $C_3$–$C_6$ cycloalkyl group can be obtained by converting a secondary amine, comprising an —$NHR_3$ group in which $R_3$ is other than hydrogen, to a tertiary amine by reaction of a compound of general formula:

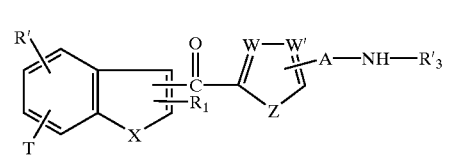

(16)

in which A, $R_1$, R', T, X, W, W' and Z have the same meaning as above and $R_{13}$ represents a linear or branched $C_1$–$C_6$ alkyl group or a $C_3$–$C_6$ cycloalkyl group, with a halide of general formula:

Hal-R"$_2$ (17)

in which Hal represents a halogen atom, preferably bromine, and $R_{12}$ represents a linear or branched $C_1$–$C_6$ alkyl group or a $C_3$–$C_6$ cycloalkyl group, the reaction taking place in the presence of a basic agent, such as an alkali metal carbonate or hydroxide, and preferably at the reflux temperature, which gives the desired compounds of formula (1) in the free base form.

The methods described above make it possible to obtain the compounds of formula (1) in the form of mixtures of isomers when one or more asymmetric carbons are present.

However, these isomers can be produced in a separate form by employing known methods, such as, for example, chromatography or precipitation.

L.—The compounds of formula (1) obtained in the free base form according to one or other of the methods described above can subsequently be converted, if necessary, to pharmaceutically acceptable salts by reaction with an appropriate organic or inorganic acid, for example oxalic, maleic, fumaric, methanesulphonic, benzoic, ascorbic, pamoic, succinic, hexamic, bismethylenesalicylic, ethanedisulphonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulphonic, p-toluenesulphonic or theophyllineacetic acid, lysine or histidine or else hydrochloric, hydrobromic, sulphuric, sulphamic, phosphoric or nitric acid.

The compounds of formula (2) can be obtained by various methods according to their chemical structure and more particularly according to the position of the R' group.

A.—The compounds of formula (2) in which R' is situated in the 5-position and represents the cyano group, a group (a) or a group (f) and $R_1$ is situated in the 2-position can be prepared according to the sequence of stages below:

a) either, a cyano derivative of general formula:

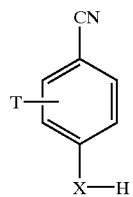
(18)

in which T and X have the same meaning as above, is treated with iodine in the presence of ammonia to form an iodo derivative of general formula:

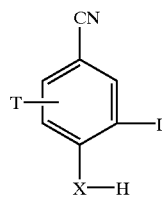
(19)

in which T and X have the same meaning as above, or, a benzoic acid derivative of general formula:

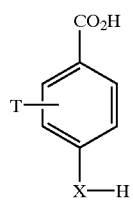
(20)

in which T and X have the same meaning as above, is treated first with an alkali metal iodide and an oxidizing agent, such as an alkali metal hypochlorite, for example sodium hypochlorite, and subsequently with an alcohol of general formula:

$R_4$—OH (21)

in which $R_4$ has the same meaning as above, which gives an iodo derivative of general formula:

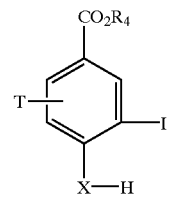
(22)

in which $R_4$, T and X have the same meaning as above, b) the iodinated derivative of formula (19) or (22) is reacted with an acetylenic derivative of general formula:

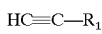
HC≡C—$R_1$ (23)

in which $R_1$ has the same meaning as above, in the presence of an appropriate catalyst, such as a palladium derivative, for example tetrakis(triphenylphosphine)palladium, and of cuprous iodide, which gives the desired compounds of formula (2).

If necessary, the preparation of the ester of formula (22) can be carried out according to the method described above but starting from an acid of formula (20) in the acyl halide form obtained after treatment of the benzoic acid derivative of formula (20) by means of a halogenating agent, for example thionyl chloride, phosgene or oxalyl chloride.

B.—The compounds of formula (2) in which R' is situated in the 6-position and represents the cyano group or a group (a) or a group (f) and $R_1$ is situated in the 2-position can be obtained as follows:

a) a compound of general formula:

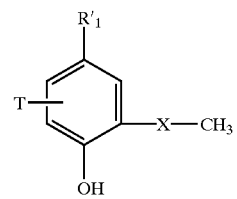
(24)

in which T and X have the same meaning as above and $R'_1$ represents the cyano group, a group (a) or a group (f), is reacted with the anhydride of trifluoromethanesulphonic acid in the presence of pyridine, to produce a compound of general formula:

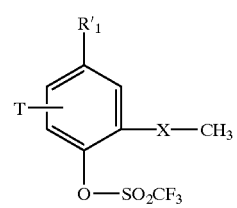
(25)

in which $R'_1$, T and X have the same meaning as above, b) the compound thus formed is reacted with an acetylenic derivative of formula (22) in the presence of an appropriate catalyst, for example a palladium derivative, such as dichlorobis(triphenylphosphine)palladium, and of an acid acceptor, such as triethylamine, to form the compounds of general formula:

(26)

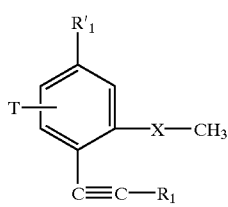

in which R'$_1$, R$_1$, T and X have the same meaning as above, c) this compound of formula (26) is then cyclized in the presence of boron tribromide at a temperature of less than −50° C., which gives the heterocyclic compounds of general formula:

(27)

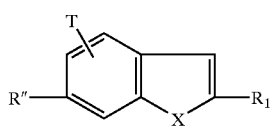

in which R$_1$, T and X have the same meaning as above and R" represents the cyano or carboxylic group, which gives either desired compounds of formula (2) where R" represents the cyano group or an acid when R" represents the carboxylic group, d) this acid is esterified with an alcohol of formula (21) or of formula (14), which gives desired compounds of the formula (2).

c.—The compounds of formula (2) in which R' is situated in the 4-position and represents the cyano group, a group (a) or a group (f) and R$_1$ is situated in the 2-position can be obtained as follows:

a) a compound of general formula:

(28)

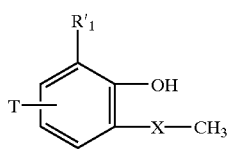

in which R'$_1$, T and X have the same meaning as above, is reacted with trifluoromethanesulphonic acid in the presence of pyridine, to produce a compound of general formula:

(29)

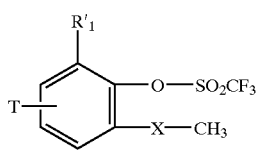

in which R$_{11}$, T and X have the same meaning as above, b) the compound thus formed is reacted with an acetylenic derivative of formula (23) in the presence of an appropriate catalyst, such as a palladium derivative, for example dichlorobis(triphenylphosphine)palladium, and of an acid acceptor, such as triethylamine, to form the compounds of general formula:

(30)

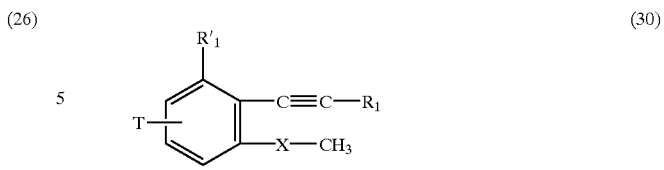

in which R'$_1$, R$_1$ and X have the same meaning as above, c) this compound of formula (30) is then cyclized in the presence of boron tribromide, which gives the heterocyclic compounds of general formula:

(31)

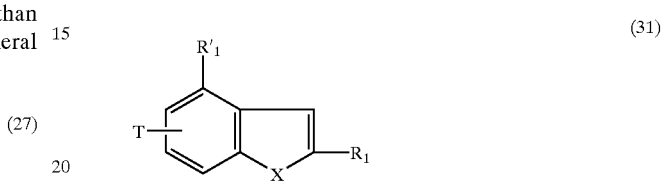

in which R'$_1$, R$_1$, T and X have the same meaning as above, which correspond to the desired compounds of formula (2).

Alternatively, the compounds of formula (2) in which R' is situated in the 5-position and represents the cyano group, a group (a) or a group (f) and R$_1$ is in the 2-position can also be prepared as follows:

I. When R' represents a group (a):

a) a benzoate of general formula:

(32)

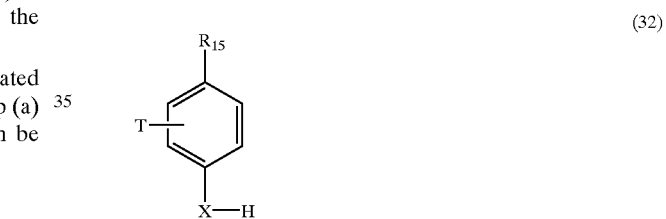

in which T and X have the same meaning as above and R$_{15}$ represents a group (a) or (f), is first treated with methanesulphonic acid in the presence of phosphorus pentoxide and hexamethylenetetraamine, to give a formyl derivative of general formula:

(33)

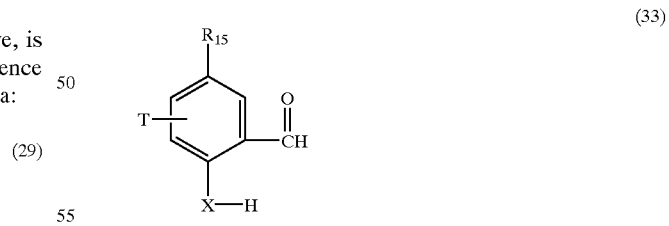

in which R$_{15}$, T and X have the same meaning as above, b) this compound of formula (33) is subsequently reacted with an ester of general formula:

(34)

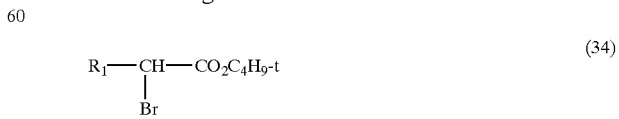

in which R$_1$ has the same meaning as above, which gives the compounds of general formula:

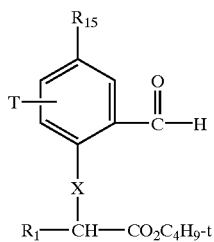
(35)

in which $R_1$, $R_{15}$, T and X have the same meaning as above, c) this ester of formula (35) is treated with formic acid or trifluoroacetic acid, which gives the acids of general formula:

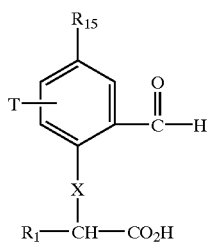
(36)

in which $R_1$, $R_{15}$, T and X have the same meaning as above, d) this compound (36) is cyclized in the presence of benzenesulphonyl chloride or p-toluenesulphonyl chloride and of an acid acceptor, such as triethylamine, which gives the desired compounds of formula (2).

II. When R' represents the cyano group:

a) a formyl derivative of general formula:

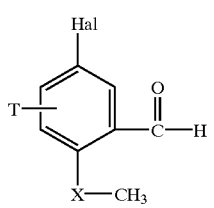
(37)

in which Hal, T and X have the same meaning as above, is first treated with zinc cyanide in the presence of an appropriate catalyst, for example a palladium derivative, such as tetrakis(triphenylphosphine)palladium, which gives the compounds of general formula:

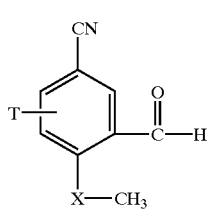
(38)

in which T and X have the same meaning as above, b) this compound of formula (38) is subsequently demethylated with lithium chloride, which gives the compounds of general formula:

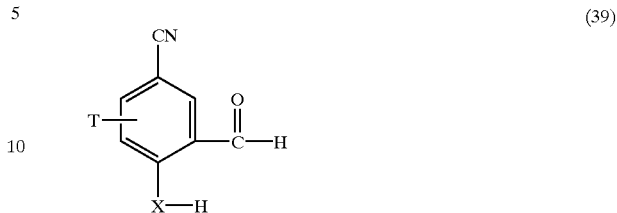
(39)

in which T and X have the same meaning as above, c) this compound of formula (39) is then treated with an ester of general formula:

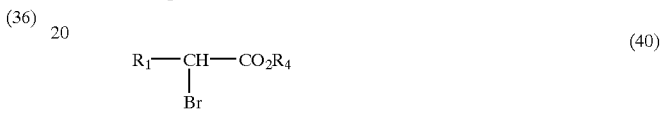
(40)

in which $R_1$ and $R_4$ have the same meaning as above, in the presence of a basic agent, such as an alkali metal carbonate, which gives the compounds of general formula:

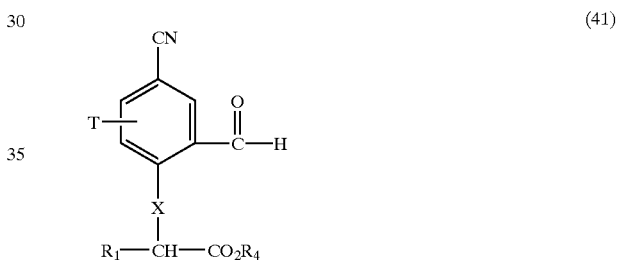
(41)

in which $R_1$, $R_4$, T and X have the same meaning as above, d) and e) this ester of formula (41) is saponified in the presence of a basic agent, such as an alkali metal hydroxide, and the acid thus obtained is cyclized in the presence of benzenesulphonyl chloride or p-toluenesulphonyl chloride and of an acid acceptor, such as triethylamine, which gives the desired compounds.

The compounds of formula (2) in which R' is situated in the 7-position and represents the cyano group, a group (a) or a group (f) and $R_1$ is situated in the 2-position can be obtained according to the sequence of stages below:

a) an alcohol of general formula:

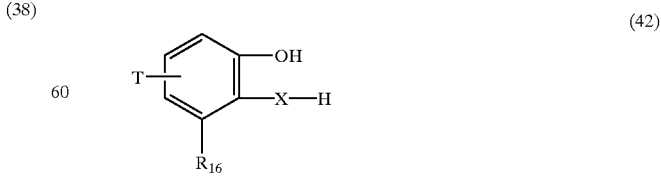
(42)

in which $R_{16}$ represents a cyano or formyl group and T and X have the same meaning as above, is treated with methyl iodide in the presence of an alkali metal hydride, to give a compound of general formula:

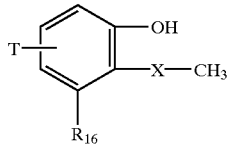

(43)

in which $R_{16}$, T and X have the same meaning as above, b) the compound thus formed is reacted with trifluoromethanesulphonic anhydride, to form a compound of general formula:

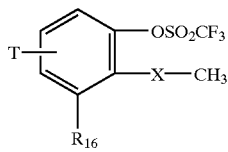

(44)

in which $R_{16}$, T and X have the same meaning as above, c) the compound thus formed is treated with a compound of the formula (23) in the presence of an appropriate catalyst, such as a palladium derivative, for example dichlorobis(triphenylphosphine)palladium which produces the compound of general formula:

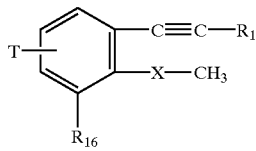

(45)

in which $R_1$, $R_{16}$, T and X have the same meaning as above, d) the compound of formula (45) thus formed is subsequently reacted:

when $R_{16}$ represents the cyano group, with lithium chloride, to form the desired compounds of formula (2) in which R' represents the cyano group, when $R_{16}$ represents the formyl group, with an alkali metal cyanide in the presence of manganous oxide and acetic acid, to give a compound of general formula:

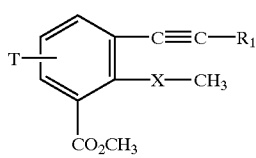

(46)

in which $R_1$, T and X have the same meaning as above, which is cyclized with lithium chloride, to give a mixture of ester and of acid of general formula:

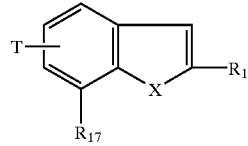

(47)

in which $R_1$, X and T have the same meaning as above and $R_{17}$ represents the methoxycarbonyl or carboxylic group, which mixture is treated with methanol in the presence of a strong acid, such as sulphuric acid, which gives the desired compounds of formula (2) in which R' represents the methoxycarbonyl group.

The other compounds of formula (2), that is to say the compounds of formula (2) in which R', situated in the 7-position, represents a group (a), with the exception of the methoxycarbonyl group, or a group (f), can be obtained by saponifying an ester of formula (2) in which R', situated in the 7-position, represents the methoxycarbonyl group, in the presence of a basic agent, such as an alkali metal hydroxide, to give a salt, which is acidified with a strong acid, such as hydrochloric acid, to give a 7-carboxybenzofuran derivative, which is esterified with an alcohol of formula (14) or an alcohol of general formula:

$R'_4$—OH    (48)

in which $R'_4$ represents a $C_2$–$C_6$ alkyl group or a $C_3$–$C_6$ cycloalkyl group, which gives the desired compounds of formula (2).

The compounds of formula (2) in which R' represents the formyl group can be prepared by oxidizing, with oxalyl chloride, an alcohol of general formula:

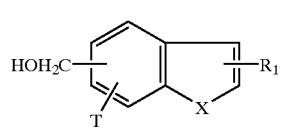

(49)

in which $R_1$, X and T have the same meaning as above, to give the desired compounds. The compounds of formula (2) in which R' represents an oxime group of formula (e) can be obtained by treating an aldehyde of general formula:

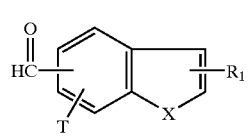

(50)

in which $R_1$, X and T have the same meaning as above, with a compound of general formula:

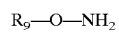

$R_9$—O—$NH_2$    (51)

in which $R_9$ has the same meaning as above, optionally in the form of its salts, in an acid-scavenging solvent, for example pyridine, to form the desired compounds.

The compounds of formula (2) in which R' represents a ketone group of formula (d) can be obtained by treating an acid of general formula:

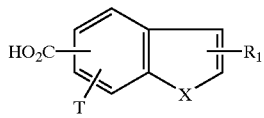

in which $R_1$, T and X have the same meaning as above, with a halogenating agent, such as thionyl chloride or oxalyl chloride, and then by reacting the acyl halide thus formed with a cadmium derivative of general formula:

in which $R_8$ has the same meaning as above, which gives the desired compounds.

The compounds of formula (3) are either known products or products which can be prepared by known methods.

For example, the compounds of formula (3) in which A represents a $C_3$–$C_5$ alkyl radical can be obtained with the sequence of stages below:

a) acylation of a compound of general formula:

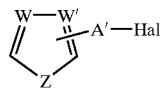

in which A', Hal, W, W' and Z have the same meaning as above, with acetyl chloride in the presence of a Lewis acid, such as aluminium chloride, to form a compound of general formula:

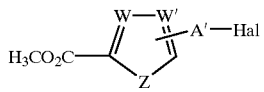

in which A', Hal, W, W' and Z have the same meaning as above, b) reaction of the compound of formula (55), first with bromine in the presence of an alkali metal hydroxide and subsequently with a strong acid, such as hydrochloric acid or sulphuric acid, to produce the acid of general formula:

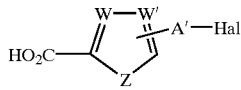

in which A', Hal, W, W' and Z have the same meaning as above, c) esterification of the acid of formula (56) or of a halide of the latter, obtained after treatment, for example, by means of thionyl chloride, this esterification being carried out by means of an alcohol of general formula:

in which $R_{18}$ represents a $C_1$–$C_4$ alkyl group, to produce an ester of general formula:

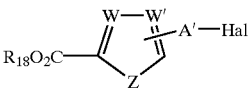

in which A', Hal, $R_{18}$, W, W' and Z have the same meaning as above, d) aminolysis of the compound of formula (58) by means of an amine of formula (6) in the presence of a basic agent, such as an alkali metal carbonate, to form the compounds of general formula:

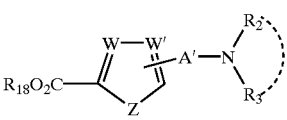

in which A', $R_2$, $R_3$, $R_{18}$, W, W' and Z have the same meaning as above, e) saponification of the compound of formula (59) by means of a basic agent, such as an alkali metal hydroxide, to form the acids of general formula:

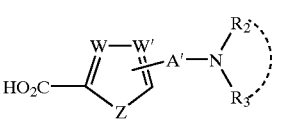

in which A', $R_2$, $R_3$, W, W' and Z have the same meaning as above, f) reaction by means of a halogenating agent, such as thionyl chloride, phosgene or oxalyl chloride, to form the desired compounds.

The compounds of formula (5) can be prepared starting from an ester of formula (1) in which R represents a group (a):

(a) by treating this ester of formula (1) at the reflux temperature of the medium by means of glycol in the presence of p-toluenesulphonic acid, to form a ketal of general formula:

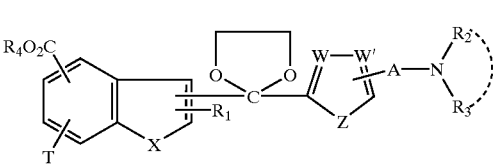

in which A, $R_1$, $R_2$, $R_3$, $R_4$, T, X, W, W' and Z have the same meaning as above, (b) by reducing this compound of formula (61) by means of an alkali metal hydride, such as lithium aluminium hydride, and in a solvent, such as an ether, to produce the desired compounds.

The compounds of formula (6) can be obtained by reacting a ketone compound of general formula:

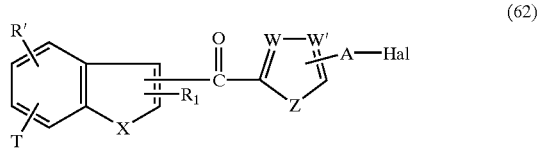

(62)

in which A, Hal, R', R₁, T, X, W, W' and Z have the same meaning as above, with sodium azide in the presence of tetrabutylammonium iodide, to form the desired compounds.

The compounds of formula (7) can be prepared starting from a compound of formula (2) by reaction of this compound with a dihalide of general formula:

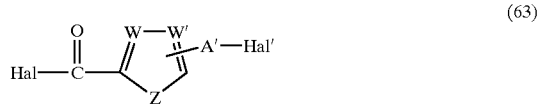

(63)

in which A', Hal, W, W' and Z have the same meaning as above and Hal' represents a halogen atom, such as chlorine or bromine, preferably bromine, the reaction taking place in the presence of a Lewis acid, such as aluminium chloride, stannic chloride, ferric chloride or silver trifluoromethanesulphonate, which gives the desired compounds.

Alternatively, the compounds of formula (7) in which R' represents a group (a) or a group (f) can be obtained by saponifying an ester of formula (7), in which R' represents a —CO₂R"₄ group in which R"₄ represents a C₁–C₁₀ alkyl group or a C₃–C₆ cycloalkyl group, in the presence of a basic agent, generally an alkali metal hydroxide, by treating the salt thus formed with a strong acid, such as hydrochloric acid, by reacting the acid thus formed with a halogenating agent, such as oxalyl chloride, and finally by esterifying the acyl halide thus formed with an alcohol of formula (13) or (14), to obtain the desired compounds.

Likewise, the compounds of formula (62) can be prepared in a manner identical to those described above for the synthesis of the compounds of formula (7).

The compounds of formula (63), for their part, can be prepared by halogenating an acid of formula (56) by means of an appropriate agent, such as thionyl chloride, phosgene or oxalyl chloride, which gives the desired compounds.

The other starting compounds or intermediates involved in the various processes described above are for the most part known compounds or compounds which can be prepared by known methods.

For example, the amines of formula (8) are known and are disclosed in patents U.S. Pat. No. 4,831,054 or EP 471 609 or being able to be prepared by the methods disclosed therein.

Benzofuran or benzothiophene derivatives which comprise an aminoalkylbenzoyl chain and which are variously substituted on the homocycle are already known. Such compounds have been disclosed, for example, in Patents or Patent Applications EP 651 998, EP 657 162, WO 95/10513 or WO 97/25033, where they are presented as possessing anticholesterolaemic, thrombin-inhibiting or oestrogen-agonist properties or inhibiting properties with respect to bone loss.

In point of fact, it has now been discovered, in the context of the invention, that benzofuran or benzothiophene derivatives comprising an aminoalkylbenzoyl chain and other groups attached to the heterocycle via a carbon atom exhibit highly advantageous pharmacological properties, in particular antiarrhythmic properties, while offering very good metabolic stability, highly acceptable solubility and very good bioavailability via the oral route.

The results of pharmacological tests carried out for the purpose of determining properties of the compounds of the invention with respect to the cardiovascular system are listed below.

I. Ventricular Arrhythmias

The aim of this test is to determine the ability of the compounds of the invention to provide protection against arrhythmias brought about by reperfusion. To this end, use was made of the method reported by Manning A. S. et al. in Circ. Res., 1984, 55, 545–548, modified as follows: Rats, divided into batches, are first anaesthetized with sodium pentobarbital (60 mg/kg via the intraperitoneal route) and then they are intubated and maintained under assisted respiration.

A cannula for intravenous administration is subsequently inserted in their right jugular veins, an intravenous dose of the compound to be studied is administered and, 5 minutes later, a ligature loop is placed around the left anterior descending coronary artery in the immediate proximity of its origin. This artery is then occluded for 5 minutes by pulling on the ends of the ligature, so as to induce reperfusion by relaxing the tension.

The arrhythmias induced by this reperfusion are then evaluated.

An analogous test was carried out by the oral route. In this case, the compound to be studied is administered 120 minutes before ligating the left anterior descending coronary artery.

The results of these tests showed that the compounds of the invention significantly protect the treated animals, ranging up to 100% at doses of between 0.3 and 10 mg/kg via the intravenous route and 10 to 90 mg/kg via the oral route.

II. Antiadrenergic Properties

The aim of this test is to determine the ability of the compounds of the invention to reduce the increase in blood pressure induced by phenylephrine (anti-α effect) and the acceleration in heart rate induced by isoprenaline (anti-β effect) in dogs anaesthetized beforehand with pentobarbital and chloralose.

For each dog, the dose of phenylephrine (5 or 10 μg/kg) which leads to an increase in the arterial pressure of between 25 and 40 mmHg and the dose of isoprenaline (0.9 or 1 μg/kg) which should lead to an increase in the heart rate of between 60 and 120 beats/minute are first determined.

The doses of phenylephrine and of isoprenaline thus determined are injected alternatively every 10 minutes and, after obtaining 2 successive reference responses, a dose of the compound to be studied is administered via the intravenous route.

Anti-α Effect

The percentage of reduction, by the compound of the invention, in the induced hypertension, in comparison with the reference hypertension obtained before injection of this compound (approximately 100 mmHg), is recorded.

Anti-β Effect

The percentage of reduction, by the compound to be studied, in the induced acceleration of the heart rate is recorded.

The results of these tests show that, at doses varying from 1 to 10 mg/kg, the compounds of the invention exhibit anti-α and/or anti-β effects which are reflected by reductions ranging from 50% to virtually 100% in the induced hypertension and/or in the induced increase of the heart rate.

III. Auricular Fibrillation

The aim of this test is to evaluate the effectiveness of the compounds of the invention with respect to auricular fibrillation induced by permanent stimulation of the vagus nerve in the anaesthetized dog according to the method described in Circulation, 1993, 88, 1030–1044. The compounds to be studied are administered at the cumulative doses of 3 to 10 mg/kg in slow intravenous infusions of 10 minutes during an episode of sustained auricular fibrillation. At the dose of 10 mg/kg, the compounds of the invention generally convert 100% of the auricular fibrillations into a sinus rhythm and prevent the reinduction thereof in 50 to 100% of cases. At this dose, significant increases in the heart period and auricular effective refractory periods for various basal values of the heart period are observed.

IV. Inhibiting Effects on the Neurohormonal System

The aim of this test is to look for inhibiting effects of the compounds of the invention with respect to vasoconstrictive effects induced by various peptides, such as noradrenaline (NA), angiotensin II (A-II), arginine vasopressin (AVP), neuropeptide Y (NPY) and endothelin (ET), and also with respect to tachycardic effects induced by isoprenaline (Iso) in the conscious rat.

An arterial catheter (right carotid artery), for the measurement of the arterial pressure, and a venous catheter (right jugular vein), for the injection of the products to be studied, are implanted, 24 hours before the test, in male Sprague Dawley rats weighing approximately 300 g. On the following day, the rats are placed in cylindrical cages and the arterial catheter is connected to a pressure sensor via a revolving joint on a pendulum. This pressure sensor is itself connected to a polygraph for recording the arterial pressure.

The action of the compounds of the invention, via the intravenous route, is then investigated with respect to vasoconstrictive effects induced by NA (1 $\mu$g/kg), A-II (100 $\mu$g/kg) and AVP (40 $\mu$g/kg) at the respective doses of either 3, 10 and 30 mg/kg or 1.3 to 10 mg/kg and solely at the dose of 10 mg/kg with respect to vasoconstrictive effects induced by NPY (6 $\mu$g/kg) and ET (0.5 $\mu$g/kg) or tachycardic effects induced by Iso (1 $\mu$g/kg). First, the various peptide agonists are dissolved in 0.9% physiological saline and the compound to be studied is dissolved in an appropriate solvent. These peptides are subsequently injected as a bolus under a volume of 0.05 ml/kg, 30 and 10 minutes before the intravenous administration of 0.1 ml/kg of a solution of the compound to be studied or of solvent. These peptide injections are subsequently repeated 10, 30, 60 and 120 minutes after the administration of the compound to be studied. According to the duration of action of the compound to be tested, these injections can optionally be extended every 30 minutes without ever exceeding a total of 5 hours.

The variations in the arterial pressure after administration of a given peptide are then evaluated by measuring, at different times, the difference between the maximum effect induced by the peptide agonist and the basal value of the arterial pressure. The results obtained show that NA, A-II, AVP, NPY and ET induce respective increases in the arterial pressure of 45±3, 40±3, 30±2 and 34±4 mmHg and Iso induces an increase in the heart rate of 209±7 beats per minute.

In addition, it is observed that the compounds of the invention antagonize in a dose-dependent fashion the vasoconstrictive effects induced by NA, A-II and AVP. They also antagonize the effects induced by NPY and by ET and the increase in the heart rate induced by Iso. At the highest doses, the maximum inhibition obtained after 15 minutes varies between 40 and 80% and the duration of action is at least greater than or equal to 30 minutes.

V. Toxicity

The toxicity of the compounds of the invention proved to be compatible with their therapeutic use.

The pharmaceutical compositions according to the invention can be presented in any form suitable for administration in human or veterinary therapy. For example, the pharmaceutical compositions of the present invention can be formulated for oral, sublingual, subcutaneous, intramuscular, intravenous, transdermal or rectal administration. As regards the administration unit, the latter can take the form, for example, of a tablet, including a sugar-coated tablet, a capsule, including a hard gelatin capsule, a powder, a suspension, a syrup or granules for oral administration, of a suppository for rectal administration or of a solution or suspension for parenteral administration.

The pharmaceutical compositions of the invention can comprise, per administration unit, for example, from 50 to 500 mg by weight of active ingredient for oral administration, from 50 to 200 mg of active ingredient for rectal administration and from 50 to 150 mg of active ingredient for parenteral administration. Depending upon the administration route chosen, the pharmaceutical or veterinary compositions of the invention will be prepared by combining at least one of the compounds of formula (1) or a pharmaceutically acceptable salt of this compound with an appropriate excipient, it being possible for the latter to be composed, for example, of at least one ingredient selected from the following substances: lactose, starches, talc, magnesium stearate, polyvinylpyrrolidone, alginic acid, colloidal silica, distilled water, benzyl alcohol or sweetening agents.

When the compositions are tablets, the latter can be treated so that they exhibit a sustained or delayed activity and that they continually release a predetermined amount of active principle.

The following nonlimiting examples illustrate the preparation of the compounds and compositions of the invention:

EXAMPLE 1

Ethyl 2-butyl-6-methyl-3-[4-[3-(dibutylamino) propyl]-benzoyl]-1-benzofuran-5-carboxylate A. 2-Methyl-4-hydroxyphenyl bromomethyl ketone 75 g (0.499 mol) of 2-methyl-4-hydroxyphenyl methyl ketone are introduced into 500 ml of dioxane and then 29.7 ml of bromine in 750 ml of dioxane are added at a temperature of less than or equal to 25° C. The mixture is stirred at ambient temperature for 2 hours and is concentrated, and the residue is recrystallized from diisopropyl ether.

In this way, 76.82 g of the desired product are obtained.

| Yield: | 67.2% |
|---|---|
| M.p.: | 130–131° C. |

B. 2-Methyl-4-hydroxybenzoic acid 76.8 g of the compound obtained in the preceding stage are introduced into 310 ml of ethyl acetate and then 70.8 ml of pyridine are added. The temperature gradually rises from 20° C. to 50° C. The reaction medium is then heated at 70° C. for 1 hour and is then allowed to return to ambient temperature.

The reaction mixture is filtered and then the isolated solid is taken up in 710 ml of 10% aqueous sodium hydroxide. The mixture is brought to reflux for 1 hour and is then allowed to return to ambient temperature. The aqueous phase is washed with diethyl ether, acidified with concentrated hydrochloric acid and extracted with ethyl acetate. The extracts are subsequently washed with water and a saturated sodium chloride solution. [lacuna] Purification is then carried out by recrystallization from water.

In this way, 41.94 g of the desired compound are obtained.

| Yield: | 82.2% |
|---|---|
| M.p.: | 178–182° C. |

C. 2-Methyl-4-hydroxy-5-iodobenzoic acid

A mixture of 7 g (46 mmol) of the compound obtained in the preceding stage, 125 ml of methanol, 3.68 g (2 equivalents) of sodium hydroxide and 15.87 g (2.3 equivalents) of sodium iodide is brought to reflux. Still at reflux, 115 ml of a sodium hypochlorite solution comprising approximately 4% of active chlorine are added over approxiamtely 30 minutes. Reflux is continued for 15 minutes and then the mixture is allowed to return to ambient temperature. 92 ml of 10% sodium thiosulphate are added, followed by 20.7 ml of concentrated hydrochloric acid. Extraction is carried out with diisopropyl ether and then washing is carried out with water to neutral pH.

In this way, 13.34 g of the desired compound are obtained in the crude form.

Yield: quantitative M.p.: between 143° C. and 150° C.

D. Ethyl 2-methyl-4-hydroxy-5-iodobenzoate 13.3 g of the compound obtained in the preceding stage are mixed in 250 ml of absolute ethanol comprising 2.5 ml of sulphuric acid. The mixture is brought to reflux for 60 hours and concentrated to dryness, and the residue is extracted with ethyl acetate. The extract is washed with water, with a sodium bicarbonate solution, with water and with a sodium chloride solution. The extract is then dissolved under hot conditions in hexane. The mixture is filtered through a filter paper to remove an oily insoluble material, the filtrate is cooled and the product is filtered off, which gives 2.79 g of the desired product. The filtrate is concentrated and chromatography is carried out on silica (eluent: dichloromethane), which gives an additional 2.12 g of the expected product.

In this way, 4.91 g of the desired product are collected.

| Yield: | 34.9% |
|---|---|
| M.p.: | 131–134° C. |

E. Ethyl 2-butyl-6-methyl-1-benzofuran-5-carboxylate

A reaction medium is prepared from 4.91 g (16 mmol) of the compound obtained in the preceding stage and from 50 ml of N,N-dimethylformamide, to which are added 2.66 g of n-hexyne, 19 ml of piperidine, 0.340 g of dichlorobis(triphenylphosphine)palladium and 0.087 g of cuprous iodide. The mixture is heated at 90° C. for 2 hours, is cooled and is concentrated. Extraction is carried out with ethyl acetate and the extract is washed with dilute hydrochloric acid and then with water. Purification is subsequently carried out by chromatography on silica (eluent: 50/50 dichloromethane/heptane).

In this way, 2.87 g of the desired compound are collected.

Yield: 68.9%

F. Ethyl 2-butyl-6-methyl-3-[4-(3-bromopropyl)benzoyl]-1-benzofuran-5-carboxylate 2.87 g (11 mmol) of the compound obtained in the preceding stage in 25 ml of 1,2-dichloroethane are added, at a temperature of less than 15° C., to 2.68 g (16.5 mmol) of ferric chloride in 70 ml of dichloroethane. 4.32 g (16.5 mmol) of 4-(3-bromopropyl)benzoyl chloride in 25 ml of 1,2-dichloroethane are then added, still at a temperature of less than 15° C. The mixture is stirred at ambient temperature for 18 hours and is then poured onto an ice/water mixture. Extraction is carried out with dichloromethane and washing is carried out, first with water to neutral pH and subsequently with a sodium chloride solution. Purification is then carried out by chromatography on silica (eluent: 70/30 dichloromethane/heptane).

In this way, 2.72 g of the desired compound are obtained.

Yield: 50.9%

G. Ethyl 2-butyl-6-methyl-3-[4-[3-(dibutylamino)propyl]benzoyl]-1-benzofuran-5-carboxylate 2.7 g (5.56 mmol) of the compound obtained in the preceding stage are dissolved in 60 ml of acetonitrile, and 1.43 g (11.1 mmol) of dibutylamine, 0.833 g (1 equivalent) of sodium iodide and 2.31 g (16.7 mmol) of potassium carbonate are added to this reaction medium. The mixture is brought to reflux for 18 hours and is poured into water. Extraction is carried out with ethyl acetate and then washing is carried out with water and a sodium chloride solution. Purification is then carried out by chromatography on silica (eluent: 98/2/0.1 dichloromethane/methanol/20% aqueous ammonia).

In this way, 2.052 g of the desired compound are obtained.

Yield: 69.14%

The following compounds were prepared in a way analogous to that described above:

Methyl 2-butyl-6-methyl-3-[4-[3-(dibutylamino)propyl]benzoyl]-1-benzofuran-5-carboxylate (Example 2).
Yield: 84.4%

Isopropyl 2-butyl-6-methyl-3-[4-[3-(dibutylamino)propyl]benzoyl]-1-benzofuran-5-carboxylate (Example 3).
Yield: 87%

EXAMPLE 4

Ethyl 2-butyl-6-methyl-3-[4-[3-(dibutylamino)propyl]benzoyl]-1-benzofuran-5-carboxylate oxalate 1.997 g (3.74 mmol) of ethyl 2-butyl-6-methyl-3-[4-[3-(dibutylamino)propyl]benzoyl]-1-benzofuran-5-carboxylate are introduced into the amount of absolute ethanol necessary in order to obtain complete dissolution. 0.337 g (1 equivalent) of oxalic acid is then added. The mixture is concentrated to dryness and triturated from diethyl ether. The product is filtered off and dried.

In this way, 2 g of the desired oxalate are obtained.

| Yield: | 85.7% |
|---|---|
| M.p.: | 158–160° C. |

The following compounds were prepared in a way analogous to that described above:

Methyl 2-butyl-6-methyl-3-[4-[3-(dibutylamino)propyl] benzoyl]-1-benzofuran-5-carboxylate oxalate (Example 5).

| Yield: | 83.8% |
|---|---|
| M.p.: | 164–166° C. |

Isopropyl 2-butyl-6-methyl-3-[4-[3-(dibutylamino)propyl] benzoyl]-1-benzofuran-5-carboxylate oxalate (Example 6).

| Yield: | 85% |
|---|---|
| M.p.: | 104–106° C. |

EXAMPLE 7

Isopropyl 2-butyl-3-[4-[3-(dibutylamino)propyl] benzoyl]-1-benzofuran-5-carboxylate fumarate 14.67 g (approximately 30 mmol) of isopropyl 2-butyl-3-[4-(3-bromopropyl)benzoyl]-1-benzofuran-5-carboxylate, 11.72 g (3 equivalents) of dibutylamine, 4.53 g (1 equivalent) of sodium iodide and 12.63 g (3 equivalents) of potassium carbonate are introduced into 300 ml of acetonitrile.

The mixture is brought to reflux for 18 hours and then evaporated. The residue is taken up in diethyl ether and washing is subsequently carried out with water and with a saturated sodium chloride solution. Purification is subsequently carried out by chromatography on silica (eluent: 100/3/0.2 dichloromethane/methanol/aqueous ammonia), which gives 11.50 g (yield: 72%) of the desired compound in the free base form.

0.533 g of the basic product thus obtained is then dissolved in 20 ml of acetone, and 0.116 g (1 equivalent) of fumaric acid is added. The mixture is evaporated and the residue is taken up in diethyl ether. The product is filtered off and dried under vacuum.

In this way, the desired fumarate is obtained.

M.p.: 132–134° C.

The following compounds were prepared in a way analogous to that described above:

Isopropyl 2-butyl-3-[4-[3-(dibutylamino)propyl]benzoyl]-1-benzofuran-5-carboxylate oxalate (Example 8).
M.p.: 131–133° C.

Isopropyl 2-butyl-6-methyl-3-[4-[3-(butylamino)propyl] benzoyl]-1-benzofuran-5-carboxylate oxalate (Example 9).

| N.M.R. | (nuclear magnetic resonance) spectrum (200 MHz) |
|---|---|
| Solvent: | DMSO (dimethyl sulphoxide) at 2.5 ppm |
| δ (ppm): | 0.6 to 1.7; unresolved peak; 20H, 4CH$_3$, 4CH$_2$ |
| | 1.85; multiplet; 2H, CH$_2$ |
| | 2.6; singlet; 3H, CH$_3$ |
| | 2.6 to 3; unresolved peak; 8H, 2CH$_2$, 2NCH$_2$ |
| | 5; septet; 1H, OCH |
| | 6.1; broad singlet; 2COOH, DOH |
| | 7.2 to 7.9; unresolved peak; 6H, aromatic $^1$H |

EXAMPLE 10

Methyl 2-butyl-3-[4-[3-(dibutylamino)propyl] benzoyl]-1-benzofuran-5-carboxylate 5 g (0.01 mol) of methyl 2-butyl-3-[4-(3-bromopropyl) benzoyl]-1-benzofuran-5-carboxylate, 2.58 g (0.02 mol) of dibutylamine, 1.5 g (0.01 mol) of sodium iodide and 4.18 g (3 equivalents) of potassium carbonate are introduced into 100 ml of acetonitrile. The mixture is brought to reflux for approximately 20 hours and extracted with diethyl ether, and the extract is washed twice with water and then with a saturated sodium chloride solution. Purification is subsequently carried out by chromatography on silica (eluent: 98/2/0.1 dichloromethane/methanol/aqueous ammonia).

In this way, 4 g of the desired compound are obtained.
Yield: 79%

EXAMPLE 11

2-Butyl-3-[4-[3-(dibutylamino)propyl]benzoyl]-1-benzofuran-5-carboxylic acid hydrochloride A reaction medium formed of 4 g of methyl 2-butyl-3-[4-[3-(dibutylamino)propyl]benzoyl]-1-benzofuran-5-carboxylate, 0.632 g (2 equivalents) of sodium hydroxide, 66 ml of dioxane, 13 ml of water and 13 ml of methanol is kept stirred at ambient temperature for 4 hours. The mixture is evaporated, the residue is taken up in water, and dilute hydrochloric acid is added to pH=4. Extraction is carried out with chloroform and the extract is washed with water and a saturated sodium chloride solution.

Purification is then carried out by chromatography on silica (eluent: 95/5 dichloromethane/methanol) to give 2.3 g (yield: 59.2%) of the desired compound.

2.3 g of the compound thus obtained are then dissolved in ethyl acetate, and a mixture of hydrochloric acid in ethyl acetate is added dropwise until the pH is acidic. The ethyl acetate is evaporated, the residue is taken up in diethyl ether and the precipitate is filtered off.

In this way, 2.18 g of the desired hydrochloride are obtained.

| Yield: | 88.2% |
|---|---|
| M.p.: | 147–149° C. |

The following compound was prepared by using the same process as above:
2-Butyl-6-methyl-3-[4-[3-(dibutylamino)propyl]benzoyl]-1-benzofuran-5-carboxylic acid oxalate (Example 12).
M.p.: 138° C.

EXAMPLE 13

2-Butyl-3-[4-[3-(dibutylamino)propyl]benzoyl]-1-benzofuran-5-carboxamide hydrochloride 3.5 g (7.1 mmol) of 2-butyl-3-[4-[3-(dibutylamino) propyl]benzoyl]-1-benzofuran-5-carboxylic acid are dissolved in 50 ml of 1,2-dichloroethane. 10 ml of thionyl chloride are subsequently added and the mixture is brought to reflux for 3 hours. The mixture is evaporated to produce a crude product, which is again taken up in 50 ml of dichloroethane comprising 10 ml of aqueous ammonia.

The reaction medium is maintained at ambient temperature for 15 hours and is then evaporated. The residue is taken up in diethyl ether and the solution is washed with water and then with a sodium chloride solution.

Purification is subsequently carried out by chromatography on silica (eluent: 95/5/0.1 dichloromethane/methanol/aqueous ammonia), which gives 1.9 g (yield: 54%) of the desired compound in the free base form.

1.9 g (3.9 mmol) of the basic compound thus obtained are subsequently dissolved in diethyl ether, a solution of hydrogen chloride in diethyl ether is added and the mixture is evaporated.

In this way, 1.6 g of the desired hydrochloride were obtained in the form of an amorphous powder.

| Yield: | 78% |
|---|---|
| N.M.R. | spectrum (200 MHz) |
| Solvent | DMSO at 2.5 ppm |
|  | DOH at 3.33 ppm |
| δ (ppm): | 0.7; triplet; 3H, $CH_3$ |
|  | 0.8; triplet; 6H, $2CH_3$ |
|  | 1.2; multiplet; 6H, $3CH_2$ |
|  | 1.5; multiplet; 6H, $3CH_2$ |
|  | 1.95; multiplet; 2H, $CH_2$ |
|  | 2.7; triplet; 4H, $2CH_2$ |
|  | 2.9; multiplet; 6H, $3NCH_2$ |
|  | 7 to 8; unresolved peak; 9H, $CONH_2$, 7 aromatic H |
|  | 10.2; broad singlet; 1H, $NH^+$ |

EXAMPLE 14

2-Butyl-3-[4-[3-(dibutylamino)propyl]benzoyl]-N,N-dimethyl-1-benzofuran-5-carboxamide Oxalate 2.8 g (5.3 mmol) of 2-butyl-3-[4-[3-(dibutylamino) propyl]benzoyl]-1-benzofuran-5-carboxylic acid are dissolved in 50 ml of dichloroethane.

10 ml of thionyl chloride are added and the mixture is brought to reflux for 3 hours.

The mixture is evaporated, the acyl chloride formed is taken up in 40 ml of dichloromethane and the solution is saturated at 5° C. with dimethylamine gas. Stirring is carried out at ambient temperature for 15 hours and the mixture is taken up in water. Separating by extracting is carried out and the aqueous layer is extracted by dichloromethane. The dichloromethane extracts are subsequently washed with water and with a sodium chloride solution and then purification is carried out by chromatography on silica (eluent: 98/2/0.2 dichloromethane/methanol/aqueous ammonia), which gives 2 g (yield: 68%) of the desired compound in the free base form.

1.82 g (3.3 mmol) of the basic compound thus obtained are then dissolved in absolute ethanol, and 0.296 g (3.3 mmol) of oxalic acid, dissolved in absolute ethanol, is added. The mixture is evaporated and the residue is crystallized from diethyl ether. The product is subsequently filtered off and then dried under vacuum.

In this way, 1.65 g of the desired oxalate are obtained.

| Yield: | 78% |
|---|---|
| M.p.: | 77–79° C. |

EXAMPLE 15

Methyl 2-butyl-3-[4-(2-aminoethyl)benzoyl]-1-benzofuran-5-carboxylate

A. Methyl 2-butyl-3-[4-(2-azidoethyl)benzoyl]-1-benzofuran-5-carboxylate 1.99 g (5 mmol) of methyl 2-butyl-3-[4-(2-chloroethyl) benzoyl]-1-benzofuran-5-carboxylate, 0.650 g (10 mmol) of sodium azide and 0.180 g (approximately 0.5 mmol) of tetrabutylammonium iodide are introduced into 10 ml of acetonitrile comprising 20 ml of N,N-dimethylformamide.

The mixture is brought to reflux for 20 hours and are then diluted in water. Extraction is carried out with diethyl ether and the extract is washed two to three times with water and then with a saturated sodium chloride solution. Purification is then carried out by chromatography on silica, dichloromethane being used as eluent.

In this way, 1.80 g of the desired compound are obtained.

Yield: 89%

M.p.: 60–62° C.

B. Methyl 2-butyl-3-[4-(2-aminoethyl)benzoyl]-1-benzofuran-5-carboxylate 1.37 g (approximately 3.4 mmol) of the compound obtained in the preceding paragraph are dissolved in 15 ml of tetrahydrofuran. The solution is cooled with an ice/water mixture and 0.89 g of triphenylphosphine is added portionwise. The ice-cold bath is removed and the mixture is stirred at ambient temperature for 3 hours. 1 ml of water is added and the mixture is stirred at ambient temperature for 16 hours. The mixture is evaporated, the residue is taken up in diethyl ether and the solution is washed with water and with a saturated sodium chloride solution. Purification is subsequently carried out by chromatography on silica (eluent: 100/7/0.5 dichloromethane/methanol/aqueous ammonia).

In this way, 1.17 g of the desired compound are obtained.

Yield: 91%

EXAMPLE 16

Methyl 2-butyl-3-[4-[2-(dibutylamino)ethyl] benzoyl]-1-benzofuran-5-carboxylate 1.12 g (approximately 3 mmol) of methyl 2-butyl-3-[4-(2-aminoethyl)benzoyl]-1-benzofuran-5-carboxylate and 0.648 g (approximately 9 mmol) of butyraldehyde are dissolved under argon in 40 ml of dichloromethane. 1.91 g (9 mmol) of sodium triacetoxyborohydride are added all at once and the mixture is stirred at ambient temperature for 18 hours. The mixture is evaporated and the residue is taken up in diethyl ether. The solution is subsequently washed with a sodium bicarbonate solution, with water and finally with a saturated sodium chloride solution.

Purification is then carried out by chromatography on silica (eluent: 100/0.5/0.15 dichloromethane/methanol/aqueous ammonia).

In this way, 1.016 g of the desired product are obtained.

Yield: 69%

EXAMPLE 17

2-Butyl-3-[4-[2-(dibutylamino)ethyl]benzoyl]-1-benzofuran-5-carboxylic acid 15.5 g (31.7 mmol) of methyl 2-butyl-3-[4-[2-(dibutylamino)ethyl]benzoyl]-1-benzofuran-5-carboxylate, 60 ml of water and 60 ml of methanol are introduced into 300 ml of dioxane.

2.59 g of sodium hydroxide are then added and the mixture is stirred at ambient temperature for approximately 20 hours, which forms the desired compound in the sodium salt form. The mixture is evaporated, the residue is taken up in water and the solution is acidified to pH=5–6 with dilute hydrochloric acid. Extraction is carried out with ethyl acetate and the extract is washed with a saturated sodium chloride solution.

In this way, 18 g of the desired compound are obtained in the crude form.

EXAMPLE 18

Isopropyl 2-butyl-3-[4-[2-(dibutylamino)ethyl]benzoyl]-1-benzofuran-5-carboxylate oxalate 3.33 g of 2-butyl-3-[4-[2-(dibutylamino)ethyl]benzoyl]-1-benzofuran-5-carboxylic acid and 5 ml of thionyl chloride are introduced into 50 ml of dichloroethane. The mixture is brought to reflux for 2 hours and evaporated. The residue is taken up in diethyl ether and the solution is again evaporated.

The residue is taken up in 50 ml of isopropanol and the mixture is brought to reflux for 16 hours. The mixture is evaporated and the residue taken up in a sodium bicarbonate solution. Extraction is carried out with diethyl ether and the extract is purified by chromatography on silica (eluent: 100/2/0.1 dichloromethane/methanol/aqueous ammonia), which gives 1.63 g (yield: 53.5%) of the desired compound in the basic form.

1.58 g of the basic compound thus obtained and 0.270 g of oxalic acid are then introduced into acetone. The mixture is evaporated, the residue is taken up in diethyl ether and the product is filtered off. It is then dried under vacuum.

In this way, 1.29 g of the desired oxalate are obtained.

| Yield: | 68.5% |
|---|---|
| M.p.: | 148–151° C. |

EXAMPLE 19

Isobutyl 2-butyl-3-[4-[3-(dibutylamino)propyl]benzoyl]-1-benzofuran-5-carboxylate Oxalate 1.58 g (3 mmol) of 2-butyl-3-[4-[3-(dibutylamino)propyl]benzoyl]-1-benzofuran-5-carboxylic acid are dissolved in 30 ml of dichloroethane, and 6 ml of thionyl chloride are added. The mixture is brought to reflux for 3 hours and is evaporated, and the residue is taken up three times in diethyl ether.

The crude product obtained is again taken up in 30 ml of isobutanol and brought to reflux for 15 hours. The mixture is evaporated and the residue is taken up in diethyl ether. The solution is washed with a dilute potassium carbonate solution, with water and finally with a sodium chloride solution. Purification is subsequently carried out by chromatography on silica (eluent: 96/4/0.1 dichloromethane/methanol/aqueous ammonia), which gives the desired compound in base form.

1.5 g (2.6 mmol) of the basic compound thus obtained are then dissolved in absolute ethanol, and 0.231 g of oxalic acid in absolute ethanol is added.

The mixture is evaporated and the residue is taken up in diethyl ether. The product is subsequently filtered off and dried under vacuum.

In this way, 1.22 g of the desired oxalate are obtained.

Yield: 73%

M.p.: 105–107° C.

EXAMPLE 20

Cyclobutyl 2-butyl-3-[4-[3-(dibutylamino)propyl]benzoyl]-1-benzofuran-5-carboxylate oxalate 3.21 g (65.3 mmol) of 2-butyl-3-[4-[3-(dibutylamino)propyl]benzoyl]-1-benzofuran-5-carboxylic acid are introduced into 50 ml of toluene. 2 ml of oxalyl chloride in 10 ml of toluene are then added at ambient temperature.

The mixture is stirred at ambient temperature and is then heated at 80° C. for 2 hours. The mixture is concentrated to dryness and the residue is taken up in diethyl ether. The mixture is again concentrated to dryness and the crude product obtained is taken up in 50 ml of dichloroethane. 0.518 g (71.8 mmol) of cyclobutanol and 0.568 g (71.8 mmol) of pyridine are then added.

The mixture is stirred at ambient temperature for 72 hours and is concentrated to dryness, and the residue is taken up in ethyl acetate. The solution is washed with water and a sodium chloride solution and then purification is carried out by chromatography on silica (eluent: 97/3/0.1 dichloromethane/methanol/aqueous ammonia), which gives 1.409 g (yield: 39.5%) of the desired compound in the base form.

1.335 g (24.5 mmol) of the basic compound thus formed are then added to the amount of methanol necessary in order to obtain complete dissolution and then 0.220 g (24.5 mmol) of oxalic acid is added. The mixture is concentrated to dryness and the residue is triturated in diethyl ether. The product is filtered off and dried.

In this way, 1.409 g of the desired compound are obtained.

| Yield: | 90.45% |
|---|---|
| M.p.: | 134–137° C. |

EXAMPLE 21

Isopropyl 2-butyl-3-[4-[3-(dibutylamino)propyl]benzoyl]-1-benzofuran-7-carboxylate oxalate A. 3-Hydroxy-2-methoxybenzaldehyde 13.08 g (0.39 mol) of sodium hydride are introduced into 300 ml of dimethyl sulphoxide and then 54 g (0.39 mol) of 2,3-dihydroxybenzaldehyde are added. The reaction medium is maintained at ambient temperature for 1 hour and then 55.35 g (26.3 ml, 0.39 mol) of methyl iodide in 60 ml of dimethyl sulphoxide are added dropwise. The mixture is maintained at ambient temperature for 18 hours and then is diluted with water. Hydrochloric acid is added, extraction is carried out with ethyl acetate and the extract is washed with an aqueous sodium chloride solution. Purification is subsequently carried out by chromatography on silica (eluent: 97/3 dichloromethane/ethyl acetate).

In this way, 27.69 g of the desired product are obtained.
M.p.: 116° C.

B. 2-Methoxy-3-(trifluoromethanesulphonyloxy)benzaldehyde 27.69 g (0.182 mol) of 3-hydroxy-2-methoxybenzaldehyde are dissolved in 290 ml of dichloromethane, and 16 g (0.2 mol) of pyridine are added. 56.42 g (33.65 ml, 0.2 mol) of trifluoromethanesulphonic anhydride in 290 ml of dichloromethane are subsequently added at a temperature of 0 to 5° C. The reaction medium is allowed to return to ambient temperature and is maintained there for 2 hours. It is evaporated and the residue is extracted with diethyl ether. The solution is washed with water, dilute hydrochloric acid, water, a sodium hydrogencarbonate solution, water and a sodium chloride solution. Purification is subsequently carried out by chromatography on silica (eluent: 90/10 dichloromethane/hexane).

In this way, 45.1 g of the desired product are obtained.
Yield: 87%

C. 2-Methoxy-3-(hexyn-1-yl)benzaldehyde 45 g (0.158 mol) of 2-methoxy-3-(trifluoromethanesulphonyloxy)benzaldehyde and 26 g (36.36 ml, 0.317 mol) of 1-hexyne are dissolved in 426 ml of N,N-dimethylformamide. 79.58 g (109.6 ml, 0.788 mol) of triethylamine and 5.53 g (0.0079 mol) of dichlorobis(triphenylphosphine)palladium are added. The reaction medium is heated at 90° C. for 2 hours, diluted with an aqueous hydrochloric acid solution and extracted with diethyl ether. The extract is washed with water and a sodium chloride solution. Purification is subsequently carried out by chromatography on silica (eluent: 5/5 dichloromethane/hexane).

In this way, 22.4 g of the desired product are obtained.
Yield: 65%

D. Methyl 2-methoxy-3-(hexyn-1-yl)benzoate 20 g (0.092 mol) of 2-methoxy-3-(hexyn-1-yl)benzaldehyde are dissolved in 840 ml of methanol, and 23.9 g of sodium cyanide, 9.24 ml of acetic acid and 187.8 g of manganous oxide are added. The reaction mixture is maintained at ambient temperature for 18 hours, is filtered and is evaporated. The residue is extracted with ethyl acetate and the extract is washed with water and with a sodium chloride solution.

In this way, 20 g of the desired compound are obtained.
Yield: 88%

E. Methyl 2-butyl-1-benzofuran-7-carboxylate 16.57 g (0.0673 mol) of methyl 2-methoxy-3-(hexyn-1-yl)benzoate are dissolved in 500 ml of N,N-dimethylformamide, and 8.56 g (0.2 mol) of lithium chloride are added. The mixture is brought to reflux for 18 hours and is then diluted with water. A potassium hydrogensulphate solution is added and extraction is carried out with ethyl acetate. The extract is subsequently washed with water and with a sodium chloride solution, which gives 16.51 g of a mixture of the desired compound and of 2-butyl-1-benzofuran-7-carboxylic acid.

17.5 g (0.078 mol) of the mixture obtained above are then dissolved in 300 ml of methanol, and 5 ml of sulphuric acid are added. The mixture is brought to reflux for 5 hours and is evaporated. The residue is extracted with ethyl acetate and the extract is washed with water and a sodium chloride solution.

Purification is subsequently carried out by chromatography on silica (eluent: 6/4 dichloromethane/hexane).

In this way, 13.24 g of the desired compound are obtained.
Yield: 73%

F. Methyl 2-butyl-3-[4-(3-bromopropyl)benzoyl]-1-benzofuran-7-carboxylate 5.29 g (0.0326 mol) of ferric chloride are introduced into 122 ml of 1,2-dichloroethane and then, at a temperature of less than or equal to 15° C., 5.05 g (0.0217 mol) of methyl 2-butyl-1-benzofuran-7-carboxylate in 61 ml of 1,2-dichloroethane are introduced. 8.2 g (0.0326 mol) of 4-(3-bromopropyl) benzoyl chloride in 61 ml of 1,2-dichloroethane are subsequently added and the mixture is maintained at ambient temperature for 18 hours. It is poured onto an ice/water mixture and extracted with dichloromethane. The extract is washed with water, dilute hydrochloric acid, water, a sodium hydrogencarbonate solution, with water and finally with a saturated sodium chloride solution. Purification is subsequently carried out by chromatography on silica (eluent: dichloromethane).

In this way, 7.95 g of the desired compound are obtained.
Yield: 82%

G. 2-Butyl-3-[4-(3-bromopropyl)benzoyl]-1-benzofuran-7-carboxylic acid 9.26 g (0.0207 mol) of methyl 2-butyl-3-[4-(3-bromopropyl)benzoyl]-1-benzofuran-7-carboxylate are dissolved in 168 ml of dioxane, and 1.65 g (0.0414 mol) of sodium hydroxide in 39 ml of water are added. 39 ml of methanol are added and the mixture is maintained at ambient temperature for 15 hours. The mixture is evaporated and the residue is taken up in hydrochloric acid to pH=1. Extraction is carried out with ethyl acetate and the extract is washed, first with water to pH=7 and subsequently with a sodium chloride solution.

In this way, 8.39 g of the desired compound are obtained.
Yield: 94%

H. Isopropyl 2-butyl-3-[4-(3-bromopropyl)benzoyl]-1-benzofuran-7-carboxylate 8.39 g (0.0193 mol) of 2-butyl-3-[4-(3-bromopropyl)benzoyl]-1-benzofuran-7-carboxylic acid are dissolved in 100 ml of toluene, and 6.5 ml of oxalyl chloride in 20 ml of toluene are added at ambient temperature. The mixture is brought to reflux for 2 hours and is then evaporated. The residue is taken up in 100 ml of isopropanol and the solution is refluxed for 15 hours and then evaporated. Purification is subsequently carried out by chromatography on silica (eluent: dichloromethane).

In this way, 4.7 g of the desired compound are obtained.
Yield: 51%

I. Isopropyl 2-butyl-3-[4-[3-(dibutylamino)propyl]benzoyl]-1-benzofuran-7-carboxylate oxalate 4.5 g (0.0095 mol) of isopropyl 2-butyl-3-[4-(3-bromopropyl)benzoyl]-1-benzofuran-7-carboxylate are dissolved in 80 ml of acetonitrile. 3.68 g (0.0285 mol) of dibutylamine are then added, followed by 1.42 g (0.0095 mol) of sodium iodide and 3.94 g (0.0285 mol) of potassium carbonate. The mixture is brought to reflux for 15 hours and is then evaporated. Extraction is carried out with diethyl ether and the extract is washed with water and a sodium chloride solution. Purification is subsequently carried out by chromatography on silica (eluent: 100/3/0.2 dichloromethane/methanol/aqueous ammonia), which gives 2.91 g of the desired compound in the free base form (yield: 57%).

2.91 g (0.00545 mol) of the basic compound thus obtained are then dissolved in absolute ethanol and then a solution of 0.490 g (0.00545 mol) of oxalic acid in absolute ethanol is added. The mixture is evaporated and the residue is taken up in diethyl ether and allowed to crystallize. The product is filtered off and dried.

In this way, 2.65 g of the desired compound are obtained.

| Yield: | 78% |
|---|---|
| M.p.: | 118–119° C. |

EXAMPLE 22

Isopropyl 2-butyl-3-[4-[3-(dibutylamino)propyl]-benzoyl]-1-benzofuran-6-carboxylate oxalate A. Isopropyl 3-methoxy-4-(trifluoromethanesulphonyloxy)benzoate 2.1 g (0.01 mol) of isopropyl 3-methoxy-4-hydroxybenzoate and 0.3 g (1.1 equivalent) of pyridine are introduced into 20 ml of dichloromethane. A solution of 3.1 g (1.1 equivalent) of trifluoromethanesulphonic anhydride in 10 ml of dichloromethane is then added dropwise between 0° and 5° C. The mixture is allowed to return to ambient temperature, stirred for 0.5 h at this temperature and evaporated. The residue is extracted with ethyl acetate and the extract is washed with water, dilute hydrochloric acid, a sodium bicarbonate solution, water and finally a saturated sodium chloride solution.

In this way, 3.22 g of the desired compound are obtained.
Yield: 94%

B. Isopropyl 3-methoxy-4-(hexyn-1-yl)benzoate 3.18 g (9.3 mmol) of the compound obtained in the preceding stage, 1.52 g (2 equivalents) of 1-hexyne, 6.5 ml (approximately 5 equivalents) of triethylamine and 0.325 g (0.05 equivalent) of dichlorobis(triphenylphosphine) palladium are introduced into 25 ml of N,N-dimethylformamide. The mixture is heated at 90° C. for 2 hours and is diluted with water, and dilute hydrochloric acid is added. Extraction is carried out with diethyl ether and the extract is washed with water and a saturated sodium chloride solution. Purification is subsequently carried out by chromatography on silica (eluent: 1/1 dichloromethane/heptane).

In this way, 1.35 g of the desired compound are obtained.
Yield: 53%

C. 2-Butyl-1-benzofuran-6-carboxylic acid 9.62 g (35 mmol) of the compound obtained in the preceding stage are introduced into 200 ml of dichloromethane and the solution is cooled to approximately −70° C. 70 ml (2 equivalents) of a 1M solution of boron tribromide in dichloromethane are then added. The mixture is allowed to return to ambient temperature and is stirred for 1 hour at ambient temperature. The mixture is cooled by means of an ice/water mixture and hydrolyzed. Extraction is carried out with dichloromethane and the extract is washed with water and a saturated sodium chloride solution. Purification is subsequently carried out by chromatography on silica (eluent: 100/3 dichloromethane/methanol).

In this way, 2.5 g of the desired compound are obtained.

| Yield: | 32.7% |
|---|---|
| M.p.: | 102–104° C. |

D. Methyl 2-butyl-1-benzofuran-6-carboxylate 2.5 g of the compound obtained in the preceding stage are introduced into 80 ml of methanol, and 1 ml of concentrated sulphuric acid is added. The mixture is brought to reflux for 6 hours and is evaporated. Extraction is carried out with diethyl ether and the extract is washed with water, a sodium bicarbonate solution, water and a saturated sodium chloride solution.

In this way, 2.60 g of the desired compound are obtained.
Yield: 98%

E. Methyl 2-butyl-3-[4-(3-bromopropyl)benzoyl]-1-benzofuran-6-carboxylate 7.30 g (1.5 equivalents) of ferric chloride are introduced into 70 ml of dichloromethane. 6.96 g (0.03 mol) of methyl 2-butyl-1-benzofuran-6-carboxylate, dissolved in 30 ml of dichloromethane, are then added at a temperature of less than or equal to 15° C., followed, under the same conditions, by 11.77 g (1.5 equivalents) of 4-(3-bromopropyl)benzoyl chloride dissolved in 30 ml of dichloromethane. The mixture is stirred at ambient temperature for 18 hours and is then poured onto an ice/water mixture. Extraction is carried out with dichloromethane and the extract is washed with water and a saturated sodium chloride solution. Purification is subsequently carried out by chromatography on silica (eluent: dichloromethane).

In this way, 7.60 g of the desired compound are obtained.
Yield: 55.4%

F. 2-Butyl-3-[4-(3-bromopropyl)benzoyl]-1-benzofuran-6-carboxylic acid 7.27 g (approximately 16 mmol) of methyl 2-butyl-3-[4-(3-bromopropyl)benzoyl]-1-benzofuran-6-carboxylate and 1.28 g (2 equivalents) of sodium hydroxide are dissolved in a mixture of 100 ml of dioxane, 30 ml of methanol and 30 ml of water. The mixture is stirred for 8 hours at ambient temperature and evaporated, and the residue is taken up in water. The solution is acidified to pH=1 to 2 and extraction is carried out with ethyl acetate. The extract is washed with water and a saturated sodium chloride solution.

In this way, the desired compound is obtained, which compound is used in the crude form.

G. Isopropyl 2-butyl-3-[4-(3-bromopropyl)benzoyl]-1-benzofuran-6-carboxylate

The 2-butyl-3-[4-(3-bromopropyl)benzoyl]-1-benzofuran-6-carboxylic acid obtained in the crude form in the preceding stage is dissolved in 100 ml of toluene and then 4.5 ml of oxalyl chloride in 15 ml of toluene are added dropwise. The reaction medium is heated at 80° C. for 2 hours and then evaporated. The residue is taken up in 100 ml of isopropanol and the mixture is brought to reflux for 2 hours. It is evaporated, the residue is taken up in water and extraction is carried out with diethyl ether. The extract is subsequently washed with a saturated sodium chloride solution and purified by chromatography on silica (eluent: dichloromethane).

In this way, 5.47 g of the desired compound are obtained.
Yield: 77.6%

H. Isopropyl 2-butyl-3-[4-[3-(dibutylamino)propyl]benzoyl]-1-benzofuran-6-carboxylate oxalate 2.7 g (approximately 6 mmol) of isopropyl 2-butyl-3-[4-(3-(bromopropyl)benzoyl]-1-benzofuran-6-carboxylate, 2.66 g (3 equivalents) of dibutylamine, 1.03 g (1 equivalent) of sodium iodide and 2.87 g (3 equivalents) of potassium carbonate are dissolved in 50 ml of acetonitrile. The reaction medium is brought to reflux for 40 hours and evaporated, and the residue is taken up in water. Extraction is carried out with diethyl ether and the extract is washed with water and a saturated sodium chloride solution. Purification is then carried out by chromatography on silica (eluent: 100/2.5/0.2 dichloromethane/methanol/aqueous ammonia), which gives 2.35 g (yield: 73.5%) of the desired compound in the basic form. 2.23 g of the basic compound thus obtained and 0.376 g of oxalic acid are subsequently mixed in acetone. The mixture is evaporated, the residue is taken up in diethyl ether and the product is filtered off and dried under vacuum.

In this way, 2.15 g of the desired compound are obtained.

| Yield: | 82.5% |
|---|---|
| M.p.: | 104–105° C. |

EXAMPLE 23

Isopropyl 2-butyl-3-[4-[3-(dibutylamino)propyl]-benzoyl]-1-benzofuran-4-carboxylate oxalate

A. Methyl 2-hydroxy-3-methoxybenzoate 25.5 g (0.152 mol) of 2-hydroxy-3-methoxybenzoic acid are introduced into 250 ml of methanol comprising 1 ml of sulphuric acid. The combined mixture is brought to reflux for 4 days and concentrated to dryness, and then the residue is extracted with ethyl acetate. The extract is subsequently washed with water, a 10% sodium carbonate solution, water and a sodium chloride solution.

In this way, 25.2 g of the desired compound are obtained.

| Yield: | 91.2% |
|---|---|
| M.p.: | 68–69° C. |

B. Methyl 2-trifluoromethanesulphonyloxy-3-methoxybenzoate 25 g (0.137 mol) of the compound obtained in the preceding stage are introduced into 200 ml of dichloromethane, and 11.93 g (0.151 mol) of pyridine are added. A mixture of 42.6 g (0.151 mol) of triflic anhydride in 200 ml of dichloromethane is then added at a temperature of 0° C. to 5° C. The mixture is stirred at ambient temperature for 3 hours and concentrated to dryness, and the residue is extracted with diethyl ether. The extract is then washed with water, dilute hydrochloric acid, water, a dilute sodium bicarbonate solution, water and a sodium chloride solution. Purification is then carried out by chromatography on silica (eluent: 5/5 dichloromethane/heptane).

In this way, 19.36 g of the desired compound are obtained.
Yield: 54.9%

C. Methyl 2-(hexyn-1-yl)-3-methoxybenzoate 19.26 g (74.9 mmol) of the compound obtained in the preceding stage are introduced into 200 ml of N,N-dimethylformamide and then 12.3 g (16.85 ml, 149.7 mmol) of 1-hexyne, 37.94 g (52.2 ml, 375 mmol) of triethylamine and 2.62 g (3.74 mmol) of dichlorobis(triphenylphosphine) palladium are added. The mixture is heated at 90° C. for 3 hours, then diluted with water and extracted with diethyl ether. The extract is then washed with dilute hydrochloric acid, water and a sodium chloride solution. Purification is then carried out by chromatography on silica (eluent: 5/5 dichloromethane/heptane and then dichloromethane).

In this way, 6.1 g of the desired compound are obtained.
Yield: 33.1%

D. Methyl 2-butyl-1-benzofuran-4-carboxylate 5.45 g (22.1 mmol) of the compound obtained in the preceding stage are introduced into 100 ml of dichloromethane. 44.5 ml of a molar solution of bromine tribromide in dichloromethane are then added at a temperature of approximately −5° C. The mixture is stirred at ambient temperature for 4 hours and then water is carefully added while keeping the temperature below 30° C. The mixture is subsequently extracted with dichloromethane and purification is carried out by chromatography on silica (eluent: dichloromethane).

In this way, 2 g of the desired compound are obtained.
Yield: 39%

E. Methyl 2-butyl-3-[4-(3-bromopropyl)benzoyl]-1-benzofuran-4-carboxylate 5.23 g (32.2 mmol) of ferric chloride are introduced into 150 ml of 1,2-dichloroethane and then a solution of 5.0 g (21.5 mmol) of methyl 2-butyl-1-benzofuran-4-carboxylate in 50 ml of 1,2-dichloroethane is added dropwise at a temperature of less than 15° C. A solution of 8.45 g (32.2 mmol) of 4-(3-bromopropyl)benzoyl chloride in 50 ml of 1,2-dichloroethane is then added dropwise at a temperature of less than 15° C. and the reaction medium is stirred for 18 hours at ambient temperture. It is poured onto a water/ice mixture and extracted with dichloromethane. The extract is washed with water to neutrality and then with a sodium chloride solution. Purification is then carried out by chromatography on silica (eluent: dichloromethane).

In this way, 7.4 g of the desired compound are obtained.
Yield: 75.3%

F. Methyl 2-butyl-3-[4-[3-(dibutylamino)propyl]benzoyl-1-benzofuran-4-carboxylate 7.4 g (16.2 mmol) of methyl 2-butyl-3-[4-(3-bromopropyl)benzoyl]-1-benzofuran-4-carboxylate are introduced into 200 ml of acetonitrile and then 2.3 g (17.8 mmol) of dibutylamine, 2.67 g (17.8 mmol) of sodium iodide and 4.48 g (32.4 mmol) of potassium carbonate are added. The reaction medium is brought to reflux for 18 hours and concentrated, and the residue is extracted with diethyl ether. The extract is washed with water and with a sodium chloride solution. Purification is subsequently carried out by chromatography on silica (eluent: 97/3/0.1 dichloromethane/methanol/aqueous ammonia).

In this way, 5.24 g of the desired compound are obtained.
Yield: 63.96%

G. 2-Butyl-3-[4-[3-(dibutylamino)propyl]benzoyl]-1-benzofuran-4-carboxylic acid 5.24 g (10.36 mmol) of methyl 2-butyl-3-[4-[3-(dibutylamino)propyl]benzoyl]-1-benzofuran-4-carboxylate are introduced into a mixture of 60 ml of dioxane and 10 ml of methanol. 0.829 g (20.72 mmol) of sodium hydroxide and 10 ml of water are then added. The mixture is stirred at ambient temperature for 18 hours and concentrated to dryness, and the residue is taken up in water. Acidification is carried out with dilute hydrochloric acid to pH=6 and extraction is carried out with ethyl acetate. The extract is then washed with water and a sodium chloride solution.

In this way, 4.48 g of the desired compound are obtained.
Yield: 88%

H. Isopropyl 2-butyl-3-[4-[3-(dibutylamino)propyl]benzoyl]-1-benzofuran-4-carboxylate oxalate 4.48 g (9.11 mmol) of 2-butyl-3-[4-[3-(dibutylamino)propyl]benzoyl]-1-benzofuran-4-carboxylic acid are introduced into 50 ml of toluene and then a solution of 4.5 ml of oxalyl chloride in 20 ml of toluene is added. The reaction medium is stirred at ambient temperature and is then brought to 80° C. for 2 hours. It is concentrated to dryness and the residue is taken up in diethyl ether and concentrated. The acyl chloride thus formed is then introduced into 300 ml of isopropanol and the reaction medium is brought to reflux for 48 hours. It is concentrated to dryness and the residue is extracted with diethyl ether. The extract is then washed with water, a sodium hydrogencarbonate solution, water and a saturated sodium chloride solution. Purification is subsequently carried out by chromatography on silica (eluent: 97/3/0.1 dichloromethane/methanol/aqueous ammonia), which gives 1.183 g (yield: 24.3%) of the desired compound in the free base form.

1.137 g (2.13 mmol) of the basic compound thus obtained are then dissolved in methanol, and 0.192 g (1 equivalent) of oxalic acid is added. The mixture is concentrated to dryness, the residue is triturated in diethyl ether, and the product is filtered off and dried.

In this way, 1.094 g of the desired compound are obtained.

| Yield: | 80% |
|---|---|
| M.p.: | 120–122° C. |

EXAMPLE 24

Isopropyl 2-butyl-3-[4-[4-(dibutylamino)butyl]benzoyl]-1-benzofuran-5-carboxylate oxalate

A. 1–Chloro-4-(4-acetylphenyl)butane 58 ml of dichloromethane are introduced into a three-necked round-bottomed flask and then 16.21 g (0.122 mol) of aluminium chloride and 9.8 q (0.125 mol) of acetyl chloride are added. 20 g (0.118 mol) of (4-chlorobutyl) benzene and 20.3 g (0.26 mol) of acetyl chloride are subsequently added dropwise at a temperature from 0° to 5° C. The reaction medium is stirred for 2 hours in an ice bath and then is poured onto an ice/water/hydrochloric acid mixture. The mixture is stirred for 15 minutes and is then extracted with dichloromethane. The extract is subsequently washed with water to neutral pH and then with sodium chloride.

In this way, 20.6 g of the desired compound are obtained.

| Yield: | 83% |
|---|---|
| B.p.: | 118–126° C. under 0.05 mmHg |

B. 4-(4–Chlorobutyl)benzoic acid 32.2 g (0.8 mol) of sodium hydroxide are dissolved in 252 ml of water, and 178 ml of dioxane are added. 15 ml (0.293 mol) of bromine are subsequently added dropwise at 0° C. and then 20.6 g (0.097 mol) of the compound obtained in the preceding stage are added between –5° C. and 0° C. The reaction medium is maintained at 0° C. for 2 hours and then hydrochloric acid is added to acidic pH. The mixture is extracted with dichloromethane and then the extract is washed with water and a sodium chloride solution. Crystallization is subsequently carried from diethyl ether.

In this way, 16.1 g of the desired compound are obtained.
Yield: 68%

C. 4-(4-Chlorobutyl)benzoyl chloride 14.65 g (0.0688 mol) of the compound obtained in the preceding stage are dissolved in 60 ml of 1,2-dichloroethane. 15 ml of thionyl chloride are then added and the mixture is brought to reflux for 3 hours and evaporated.

In this way, 7.45 g of the desired compound are obtained.

| Yield: | 47% |
|---|---|
| B.p.: | 129–130° C. under 0.05 mmHg |

D. Methyl 2-butyl-3-[4-(4-bromobutyl)benzoyl]-1-benzofuran-5-carboxylate 5.23 g of ferric chloride are introduced into 122 ml of 1,2-dichloroethane, and 7.45 g (0.0322 mol) of methyl 2-butyl-1-benzofuran-5-carboxylate in 61 ml of 1,2-dichloroethane are added at a temperature of less than or equal to 15° C. 5 g (0.0217 mol) of the compound obtained in the preceding stage in 61 ml of dichloromethane are subsequently added. The reaction medium is maintained at ambient temperature for 18 hours and is then poured onto an ice/water mixture. Extraction is carried out with dichloromethane and then the extract is washed with water, dilute hydrochloric acid, a sodium hydrogencarbonate solution, water and a saturated sodium chloride solution. Purification is subsequently carried out by chromatography on silica (eluent: dichloromethane).

In this way, 7 g of the desired compound are obtained.
Yield: 76%

E. 2-Butyl-3-[4-(4-bromobutyl)benzoyl]-1-benzofuran-5-carboxylic acid 6.7 g (0.0157 mol) of the compound obtained in the preceding stage are dissolved in 127 ml of dioxane, and 1.256 g (0.0314 mol) of sodium hydroxide, dissolved in 30 ml of water, are added. 30 ml of methanol are added and the reaction medium is maintained at ambient temperature for 18 hours. It is evaporated and the residue is acidified with hydrochloric acid to pH=2. Extraction is carried out with ethyl acetate. The extract is subsequently washed with water and then a saturated sodium chloride solution.

In this way, 7.06 g of the desired compound are obtained.
Yield: 100%

F. Isopropyl 2-butyl-3-[4-(4-bromobutyl)benzoyl]-1-benzofuran-5-carboxylate 7.06 g (0.0175 mol) of the compound obtained in the preceding stage are dissolved in 90 ml of toluene, and 6 ml of oxalyl chloride, dissolved in 18 ml of toluene, are added dropwise at ambient temperature. The mixture is brought to reflux and then evaporated. The residue is taken up in diethyl ether and the mixture is evaporated. The residue is again taken up in 100 ml of isopropanol and brought to reflux. The mixture is evaporated and the residue is purified by chromatography on silica (eluent: dichloromethane).

In this way, 3.94 g of the desired compound are obtained.
Yield: 50%

G. Isopropyl 2-butyl-3-[4-[4-(dibutylamino)butyl]benzoyl]-1-benzofuran-5-carboxylate oxalate 3.7 g (0.0081 mol) of the compound obtained in the preceding stage are dissolved in 80 ml of acetonitrile and then 3.14 g (0.0243 mol) of dibutylamine, 1.21 g (0.0081 mol) of sodium iodide and 3.36 g (0.0243 mol) of potassium carbonate are added. The mixture is brought to reflux and then evaporated. The residue is taken up in diethyl ether and the solution is then washed with water and a sodium chloride solution. Purification is subsequently carried out by chromatography on silica (eluent: 98/2/0.1 dichloromethane/methanol/aqueous ammonia), which gives 2 g (yield: 45%) of the desired compound in the basic form.

1.59 g (0.0029 mol) of the basic compound thus obtained are then dissolved in absolute ethanol and a solution of 0.261 g (0.0029 mol) of oxalic acid is added. The mixture is evaporated and the residue is taken up in diethyl ether. Crystallization is subsequently carried out from diethyl ether.

In this way, 1.55 g of the desired compound are obtained.

| | |
|---|---|
| Yield: | 84% |
| M.p.: | 79–80° C. |

EXAMPLE 59

2-Butyl-3-[4-(3-(dibutylamino)propyl)benzoyl)-benzofuran-5-carboxylic acid methoxymethylamide oxalate

A. 3-[4-(3-Bromopropyl)benzoyl]-2-butylbenzofuran-5-carboxylic acid chloride 2.8 g of 3-[4-(3-bromopropyl)benzoyl]-2-butylbenzofuran-5-carboxylic acid, 2.8 ml of SOCl$_2$ (thionyl chloride) and 30 ml of DCM (dichloromethane) are mixed, which mixture is brought to reflux for 3 hours. It is evaporated and the residue is taken up several times in ether to remove the excess SOCl$_2$. The mixture is evaporated to dryness.

In this way, 3 g of the desired compound are obtained.

B. 3-[4-(3-Bromopropyl)benzoyl]-2-butylbenzofuran-5-carboxylic Acid Methoxymethylamide 1.9 g of dimethylhydroxylamine are added under cold conditions to 3 g of the compound obtained in the preceding stage A in EtCl$_2$. 1.9 g of diisopropylethylamine (DIPEA) in DCM are added dropwise over 20 minutes. The mixture is allowed to return to ambient temperature. The DCM is evaporated and then the residue is taken up in water and ethyl acetate. Extraction is carried out three times with ethyl acetate and then the extracts are washed twice with water and then with an aqueous NaCl solution. The extracts are dried over Na$_2$SO$_4$ and concentrated, and then the residue is purified by chromatography on silica (eluent: ethyl acetate/DCM).

In this way, 2.2 g of the desired compound are obtained.

C. 2-Butyl-3-[4-(3-(dibutylamino)propyl)benzoyl]benzofuran-5-carboxylic acid methoxymethylamide 2.2 g of the compound obtained in the preceding stage B, 3 molar equivalents of dibutylamine, 750 mg of sodium iodide, 2.3 g of potassium carbonate and 50 ml of acetonitrile are mixed. The mixture is brought to reflux for 16 hours. As the reaction is not complete, one equivalent of dibutylamine is added (a total of 3 ml for this reaction) and the mixture is left to react for 16 hours at reflux. It is evaporated to dryness and the residue is taken up in water and ether. Extraction is carried out three times with ether and the extracts are washed with water and a saturated aqueous NaCl solution. The extracts are dried over Na$_2$SO$_4$ and concentrated, and then the residue is purified by chromatography on silica (eluent: ethyl acetate/DCM, up to 30% of ethyl acetate, and then: methanol/DCM).

In this way, 1.977 g of the desired compound are obtained.

E. 2-Butyl-3-[4-(3-(dibutylamino)propyl)benzoyl]benzofuran-5-carboxylic acid methoxymethylamide oxalate 1.977 g of the compound obtained in the preceding stage C are mixed with one molar equivalent of oxalic acid in methanol. The methanol is subsequently evaporated and the residue is triturated in ether. The product is filtered off.

In this way, 1.3 g of the desired compound are obtained.

EXAMPLE 74

Isopropyl 2-butyl-3-[4-(3-dibutylamino-2-hydroxypropyl)benzoyl]benzofuran-5-carboxylate oxalate

A. 3-(4-Allylbenzoyl)-2-butylbenzofuran-5-carboxylic acid 1.7 g of NaOH pellets are added to 8.1 g of methyl 3-(4-allylbenzoyl)-2-butylbenzofuran-5-carboxylate in 40 ml of methanol, 200 ml of dioxane and 40 ml of water. The mixture is stirred at ambient temperature for 24 hours. It is neutralized to pH 7 with concentrated hydrochloric acid and then evaporated. Water is added and the acid is regenerated with concentrated hydrochloric acid. Extraction is carried out three times with ether and the extracts are washed with water and then with an aqueous NaCl solution. They are dried over Na$_2$SO$_4$ and then concentrated.

7.5 g of the crude product are thus obtained, which product is used as is for the following stage.

B. Isopropyl 3-(4-allylbenzoyl)-2-butylbenzofuran-5-carboxylate 7.5 ml of $SOCl_2$ are added to 7.5 g of the product obtained in the preceding stage A in 100 ml of DCM. The mixture is heated at 45° C. for 3 hours and then evaporated. The residue is taken up in ether and then the mixture is evaporated to dryness. 150 ml of isopropanol are subsequently added and the mixture is brought to reflux at 100° C. for 2 hours. It is evaporated. The residue is taken up in water and DCM. Extraction is carried out with DCM and the extracts are washed with water. They are dried over $Na_2SO_4$ and then concentrated, and the residue is purified by chromatography on silica (eluent: hexane/DCM).

In this way, 5.55 g of the crude product are obtained, which product is used as is for the following stage.

C. Isopropyl 2-butyl-3-(4-(oxiranylmethyl)benzoyl)benzofuran-5-carboxylate 3.3 g of 3-chloroperbenxoic acid are added at ambient temperature to 5.55 g of the product obtained in the preceding stage B in 50 ml of DCM. The mixture is stirred at ambient temperature for 16 hours. A further 660 mg (20%) of 3-chloroperbenzoic acid are added and the mixture is stirred at ambient temperature for 60 hours. The insoluble material is filtered off and then the filtrate is washed with water. It is dried over $Na_2SO_4$ and concentrated, and then the residue is purified by chromatography on silica (eluent: hexane/DCM).

In this way, 1.5 g of the desired compound were obtained.

D. Isopropyl 2-butyl-3-[4-(3-dibutylamino-2-hydroxypropyl)benzoyl]benzofuran-5]-carboxylate 1.5 g of the compound obtained in the preceding stage C are mixed with 1.5 g of dibutylamine and 30 ml of acetonitrile, which mixture is brought to 60° C. for 60 hours. It is evaporated and the residue is placed directly on a silica column for purification (eluent: DCM/ethyl acetate and then DCM/methanol).

In this way, 899 mg of the desired compound are obtained.

E. Isopropyl 2-butyl-3-[4-(3-dibutylamino-2-hydroxypropyl)benzoyl]benzofuran-5-carboxylate oxalate 134 mg of oxalic acid and 899 mg of the compound obtained in the preceding stage D are dissolved in isopropanol. Mixing is carried out and the mixture is evaporated. The residue is taken up and triturated in ether. The product is filtered off.

In this way, 771 mg of the desired compound are obtained.

EXAMPLE 89

Isopropyl 2-butyl-3-[4-(2-dibutylaminoethoxymethyl)benzoyl]benzofuran-5-carboxylate oxalate

A. Methyl 3-(4-(bromomethyl)benzoyl)-2-butylbenzofuran-5-carboxylate 60 ml of $SOCl_2$ (thionyl chloride) and 390 ml of DCM (1,2-dichloromethane) are added to 25 g of 4-(bromomethyl) benzoic acid. The mixture is heated at 50° C. for 4 hours and 30 minutes. It is evaporated and the residue is taken up in diethyl ether. 27.5 g of the acid chloride are thus obtained, to which acid chloride are added, under cold conditions, 20 ml of $SnCl_4$, 400 ml of $EtCl_2$ and 14 g of methyl 2-butylbenzofuran-5-carboxylate. The mixture is heated at 49° C. for 18 hours. It is poured onto ice. Extraction is carried out three times with DCM. The extracts are washed with water and with $NaHCO_3$. They are dried over $Na_2SO_4$. They are concentrated and then the residue is purified by chromatography over silica (eluent: hexane/DCM).

In this way, 16.85 g of the desired compound are obtained.

B. Methyl 2-butyl-3-[4-(2-chloroethoxymethyl)-benzoyl]benzofuran-5-carboxylate and 2-chloroethyl 2-butyl-3-[4-(2-chloroethoxymethyl)benzoyl]-benzofuran-5-carboxylate 3.5 g of the compound obtained in the preceding stage A, 3.35 g of $AgClO_4$ and 25 ml of 2-chloroethanol are mixed, which mixture is heated at 90° C. for 1 hour. DCM is subsequently added and then the mixture is filtered. The filtrate is washed with water and then dried over $Na_2SO_4$. It is concentrated and then the residue is purified by chromatography on silica (eluent: hexane/DCM).

2.5 g of a product, including the desired compound, are thus obtained.

C. 2-Butyl-3-[4-(2-chloroethoxymethyl)benzoyl]benzofuran-5-carboxylic acid 2.5 g of the product obtained in the preceding stage B, 10 ml of methanol, 50 ml of dioxane, 10 ml of water and 466 mg of NaOH are mixed. The mixture is stirred for 16 hours at ambient temperature. Water is added and then the impurities are extracted with ether. The acid is regenerated with concentrated hydrochloric acid until an acidic pH is obtained. Extraction is subsequently carried out three times with ethyl acetate and the extracts are washed with water and then with a saturated aqueous NaCl solution. The extracts are dried over $Na_2SO_4$ and then concentrated.

In this way, 2.2 g of the desired compound are obtained.

D. Isopropyl 2-butyl-3-[4-(2-chloroethoxymethyl)benzoyl]benzofuran-5-carboxylate 2.2 g of the compound obtained in the preceding stage C, 3 ml of $SOCl_2$ and 40 ml of DCM are mixed, which mixture is heated at 45° C. for 1 hour 30 minutes. The mixture is evaporated, the residue is taken up in ether and then the mixture is concentrated to dryness. 2.1 g of product are thus obtained, which product is mixed with 50 ml of isopropanol. The mixture is brought to reflux for 2 hours and then evaporated, and the residue is purified by chromatography on silica (eluent: hexane/DMC).

In this way, 1.68 g of the desired compound are obtained.

E. Isopropyl 2-butyl-3-[4-(2-dibutylaminoethoxymethyl)benzoyl]benzofuran-5-carboxylate 1.68 g of the compound obtained in the preceding stage D, 551 mg of sodium iodide, 1.85 ml of dibutylamine, 1.52 g of potassium carbonate and 40 ml of acetonitrile are mixed. The mixture is heated at 110° C. for 48 hours. It is taken up in water and ethyl acetate. Extraction is carried out three times with ethyl acetate and the extracts are washed with water. They are dried over $Na_2SO_4$ and then concentrated, and the residue is purified by chromatography on silica (eluent: methanol/DCM).

In this way, 1.6 g of the desired compound are obtained.

F. Isopropyl 2-butyl-3-[4-(2-dibutylaminoethoxymethyl)benzoyl]benzofuran-5-carboxylate oxalate 1.6 g of the compound obtained in the preceding stage E are mixed with 262 mg of oxalic acid in methanol. The solvent is evaporated, the residue is triturated in ether and then the product is filtered off.

1.39 g of the desired compound are thus obtained.

EXAMPLE 97

Isopropyl 3-[4-(3-(dibutylamino)propyl)benzoyl]-2-(4-hydroxybutyl)benzofuran-5-carboxylate oxalate

A. tert-Butyl(hex-5-ynyloxy)diphenylsilane 49.1 g (0.178 mol) of tert-butyldiphenylsilyl chloride in 100 ml of DMF are introduced at ambient temperature into 100 ml of DMF (N,N-dimethylformamide), 15.91 g (0.162 mol) of hex-5-yn-1-ol and 24.27 g (0.356 mol) of imidazole. The mixture is stirred at ambient temperature for 4 hours and is then poured into water, and extraction is carried out with ethyl acetate, followed by washing with water.

In this way, 59.19 g of the desired compound are obtained.

B. Methyl 2-[4-(tert-butyldiphenylsilanyloxy)butyl]benzofuran-5-carboxylate 24.2 g (0.0719 mol) of the compound obtained in the preceding stage A, 10 g (0.036 mol) of methyl 4-hydroxy-3-iodobenzoate, 400 ml of DMF, 32.8 ml of piperidine, 819 mg of dichlorobis(triphenylphosphine)palladium and 210 mg of cuprous iodide are mixed. This mixture is heated at 90° C. for 4 hours. It is concentrated to dryness, the residue is subsequently extracted with ethyl acetate, the extract is then washed with water, a sodium chloride solution and dilute hydrochloric acid, and then purification is carried out by chromatography on silica (eluent: DCM).

In this way, 13.50 g of the desired compound are obtained.
Yield: 77.1%

C. Methyl 3-[4-(3-bromopropyl)benzoyl]-2-{4-[4-(3-bromopropyl)benzoyloxy]butyl}benzofuran-5-carboxylate 8.06 g (0.0166 mol) of the compound obtained in the preceding stage B, dissolved in 200 ml of EtCl$_2$ (1,2-dichloroethane), are added to a mixture of 6.62 g (0.0497 mol) of aluminium chloride and 100 ml of EtCl$_2$, followed by 13.06 g (0.0497 mol) of 4-(3-bromopropyl)benzoic acid chloride and 100 ml of EtCl$_2$. The mixture is brought to 35° C. for 72 hours. It is subsequently poured onto water and ice and then extracted with DCM, the extract is washed with water and then purification is carried out by chromatography on silica (eluent: DCM and methanol at 98/2).

In this way, 3.3 g of the desired compound are obtained.
Yield: 28.46%

D. 3-[4-(3-Bromopropyl)benzoyl]-2-(4-hydroxybutyl)benzofuran-5-carboxylic acid 759 mg of NaOH and 10 ml of water are added to a mixture of 3.30 g (0.0472 mol) of the compound obtained in the preceding stage C, 50 ml of dioxane and a few ml of methanol to bring the dissolution to completion. The mixture is stirred at ambient temperature for 4 hours. It is concentrated to dryness. The residue is taken up in distilled water. Acidification is carried out with dilute hydrochloric acid. Extraction is subsequently carried out with ethyl acetate and the extract is washed with water, and then purification is carried out by chromatography on silica (eluent: DCM/methanol).

In this way, 1.156 g of the desired compound are obtained.
Yield: 53.3%

E. Isopropyl 3-[4-(3-bromopropyl)benzoyl]-2-(4-hydroxybutyl)benzofuran-5-carboxylate 1.094 g (0.0238 mol) of the compound obtained in the preceding stage D, 50 ml of acetonitrile, 1.156 g (0.0357 mol) of caesium carbonate and 4.06 g (0.0238 mol) of isopropyl iodide are mixed, which mixture is brought to reflux for 2 hours and 30 minutes. The mixture is filtered through a sintered glass filter and then the filtrate is concentrated to dryness. The concentrated product is taken up in ethyl acetate. The solution is washed with dilute NaHCO$_3$, with water and an NaCl solution and then purification is carried out by chromatography on silica (eluent: DCM/methanol).

In this way, 699 mg of the desired compound are obtained.

Yield: 58.6%

F. Isopropyl 3-[4-(3-(dibutylamino)propyl)benzoyl]-2-(4-hydroxybutyl)benzofuran-5-carboxylate 869 mg (0.00173 mol) of the compound obtained in the preceding stage E, 20 ml of acetonitrile, 672 mg (0.0052 mol) of dibutylamine, 718 mg (0.0052 mol) of potassium carbonate and 259 mg (0.0073 mol) of sodium iodide are mixed, which mixture is brought to reflux for 5 hours. It is concentrated to dryness and then the residue is extracted with ethyl acetate. The extract is washed with water and with a saturated NaCl solution and then purification is carried out by chromatography on silica (eluent: DCM/methanol/NH$_4$OH).

In this way, 482 mg of the desired compound are obtained.

Yield: 50.67%

G. Isopropyl 3-[4-(3-(dibutylamino)propyl)benzoyl]-2-(4-hydroxybutyl)benzofuran-5-carboxylate oxalate A mixture comprising 443 mg (0.806 mmol) of the compound obtained in the preceding stage F, an amount of methanol sufficient for complete dissolution and 73 mg (0.806 mmol) of oxalic acid is prepared. It is concentrated to dryness and the residue is placed under isopropyl ether. The product is filtered off and dried.

In this way, 463 mg of the desired compound are obtained.

Yield: 89.8%

By using the processes described in the preceding examples, the compounds listed below were prepared. As regards the compounds of Examples 25, 32, 33, 42, 45, 46 and 58, the results of the N.M.R. spectra have been listed.

| | | | |
|---|---|---|---|
| 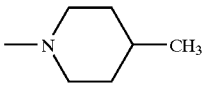 | Oxalate m.p.: 150° C. | 31 | |
| 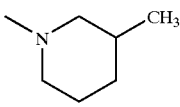 | Hydrochloride Solid | 32 | |
| 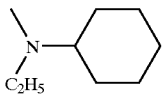 | Oxalate Amorphous powder | 33 | |
| 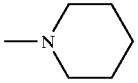 | Hydrochloride M.p.: 149° C. | 34 | |
| 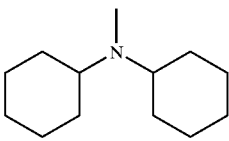 | Oxalate White solid M.p.: 127° C. | 35 | |
| 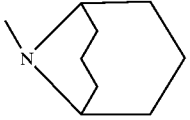 | Hydrochloride White solid M.p.: 209° C. | 36 | |
| 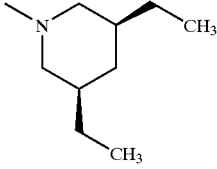 | Hydrochloride White solid M.p.: 135° C. | 37 | |
| 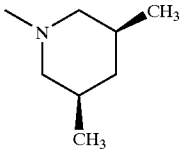 | Hydrochloride White powder M.p.: 167° C. | 38 | |
|  | Hydrochloride M.p.: 146° C. | 39 | |
| 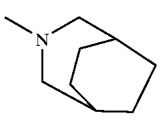 | Oxalate White powder M.p.: 160° C. | 40 | |
| 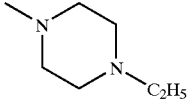 | Dioxalate White powder M.p.: 227–228° C. | 48 | |
| 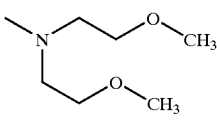 | Oxalate White powder M.p.: 74–75° C. | 49 | |

-continued

| Structure | Characteristics | Example |
|---|---|---|
| N(CH3)-(CH2)3-CF3, with N-CH2CH2CH3 | Oxalate Powder M.p.: 146° C. | 50 |
| N(CH3)(CH2CH2CH3)(CH2CH2CH2CH3) | Oxalate White solid M.p.: 97–98° C. | 51 |
| 1,2,5-trimethylpiperazine | Dioxalate Powder M.p.: 90–93° C. | 52 |
| N(CH3)(CH2CH2CH3)(CH2CH2CH3) | Oxalate Solid M.p.: 109–11° C. | 53 |
| N(CH3)(CH2)2-pyrrolidinyl, with CH3 | Dioxalate Powder | 54 |
| N(CH3)(CH2)4F with (CH2)4F | Oxalate Powder M.p.: 90–93° C. | 55 |
| N-methyl hexahydropyrrolizine | Dioxalate Powder M.p.: 148° C. | 56 |

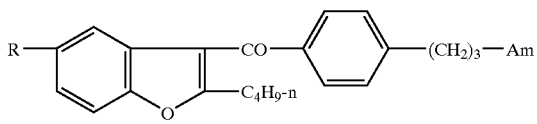

| R | Am | Characteristics | Example |
|---|---|---|---|
| H3CO2C— | —N-piperidine | Hydrochloride M.p.: 153° C. | 41 |
| H5C2O2C— | —N(C4H9)2 | Oxalate Solid | 42 |
| H7C3O2C— | —N(C4H9)2 | Oxalate Solid M.p.: 119° C. | 43 |
| cyclopentyl-O2C— | —N(C4H9)2 | Oxalate M.p.: 132° C. | 44 |
| (H4C2)2N—CO— | —N(C4H9)2 | Oxalate Solid | 45 |
| i-H7C3NH—CO— | —N(C4H9)2 | Oxalate Amorphous solid | 46 |
| N≡C— | —N(C4H9)2 | Oxalate White solid | 57 |

-continued

| Compound | | Characteristics | Example |
|---|---|---|---|
| 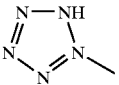 | —N(C₄H₉)₂ | Oxalate<br>Amorphous white solid | 58 |
| 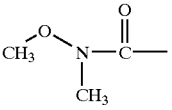 | —N(C₄H₉)₂ | Oxalate<br>Powder<br>M.p.: 82–83° C. | 59 |
| (CH₃)₂N(CH₂)₂O—C(=O)— | —N(C₄H₉)₂ | Oxalate<br>White solid<br>M.p.: 138–141° C. | 60 |
| HOCH₂— | —N(C₄H₉)₂ | Oxalate<br>Solid<br>M.p.: 117–119° C. | 61 |
| HOC— | —N(C₄H₉)₂ | Oxalate<br>Solid<br>M.p.: 114–116° C. | 62 |
| 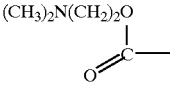 | —N(C₄H₉)₂ | Oxalate<br>Powder<br>M.p.: 94° C. | 63 |
| H₃CO₂C— | 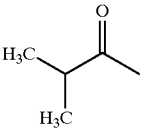 | Oxalate<br>Powder<br>M.p: 107–109° C. | 64 |

The compounds listed below were also prepared. As regards the compounds of Examples 81 and 92, the results of the N.M.R. spectra have also been listed.

| Compound | Characteristics | Example |
|---|---|---|
| 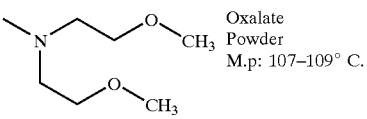 | Oxalate<br>White solid<br>M.p.: 155–157° C. | 65 |
| 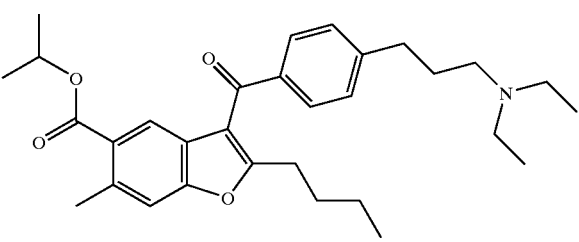 | Oxalate<br>Powder<br>M.p.: 128–130° C. | 66 |

| Compound | Characteristics | Example |
|---|---|---|
| | Oxalate<br>Solid<br>M.p.: 155–157° C. | 67 |
| | Oxalate<br>Solid<br>M.p.: 119–121° C. | 68 |
| | Oxalate<br>White solid<br>M.p.: 124–126° C. | 69 |
| | Oxalate<br>White solid<br>M.p.: 124–126° C. | 70 |
| | Oxalate<br>White solid<br>M.p.: 124–126° C. | 71 |
| | Oxalate<br>White solid<br>M.p.: 105–107° C. | 72 |

| Compound | Characteristics | Example |
|---|---|---|
| | Oxalate<br>Solid<br>M.p.: 75–78° C. | 73 |
| | Oxalate<br>White solid<br>M.p: 90–91° C. | 74 |
| | Oxalate<br>White solid<br>M.p.: 96–97° C. | 75 |
| | Oxalate<br>White solid<br>M.p.: 107–108° C. | 76 |
| | Oxalate<br>White powder<br>M.p.: 107–108° C. | 77 |
| | Oxalate<br>Powder<br>M.p.: 85–88° C. | 78 |

-continued
| Compound | Characteristics | Example |
|---|---|---|
| 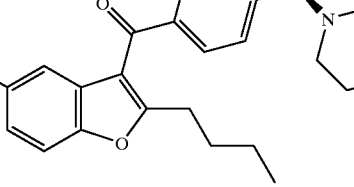 | Oxalate<br>Powder<br>M.p.: 150–151° C. | 79 |
| 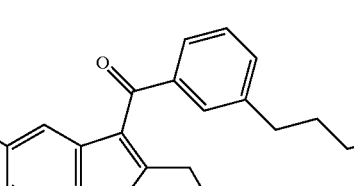 | Oxalate<br>Solid<br>M.p.: 87–90° C. | 80 |
| 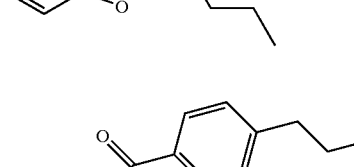 | Oxalate<br>Amorphous solid | 81 |
| 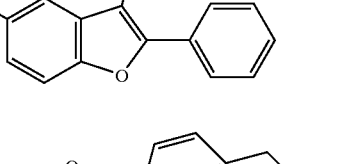 | Dioxalate<br>Crystals<br>M.p.: 220–221° C. | 82 |
| 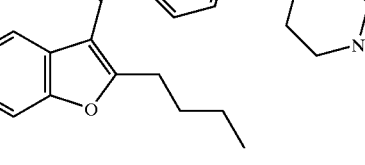 | Oxalate<br>White solid<br>M.p.: 107–108° C. | 83 |
| 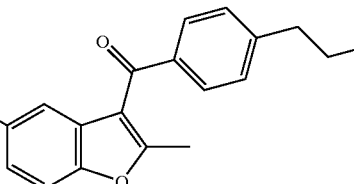 | Dioxalate<br>Solid<br>M.p.: 222–224° C. | 84 |

| Compound | Characteristics | Example |
|---|---|---|
|  | Oxalate<br>White powder<br>M.p.: 105° C. | 85 |
|  | Oxalate<br>White solid<br>M.p.: 107–108° C. | 86 |
|  | Oxalate<br>Solid<br>M.p.: 86–89° C. | 87 |
|  | Oxalate<br>Solid<br>M.p.: 92–93° C. | 88 |
|  | Oxalate<br>Powder<br>M.p.: 73° C. | 89 |
|  | Oxalate<br>Powder<br>M.p.: 100° C. | 90 |

-continued
| Compound | Characteristics | Example |
|---|---|---|
| 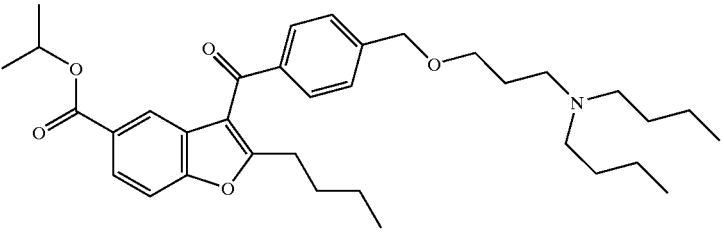 | Oxalate<br>Powder<br>M.p.: 73–74° C. | 91 |
| 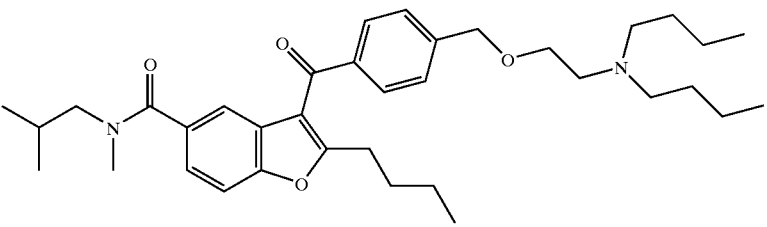 | Oxalate<br>Amorphous<br>powder | 92 |
| 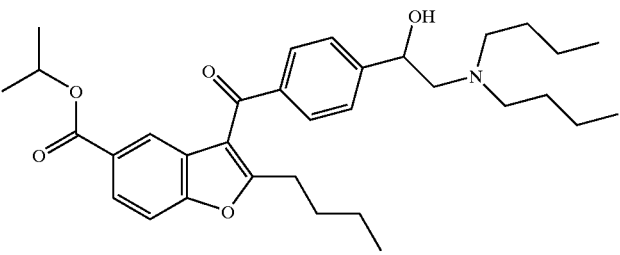 | Oxalate<br>White powder<br>M.p.: 134–135° C. | 93 |
| 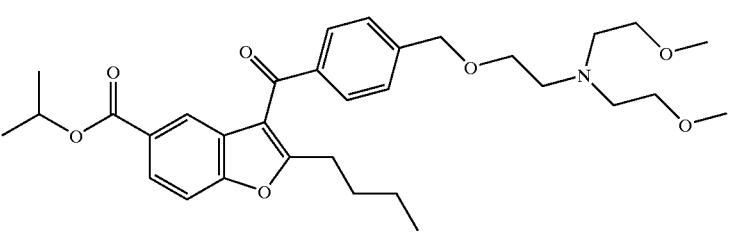 | Oxalate<br>Powder<br>M.p.: 93–94° C. | 94 |
| 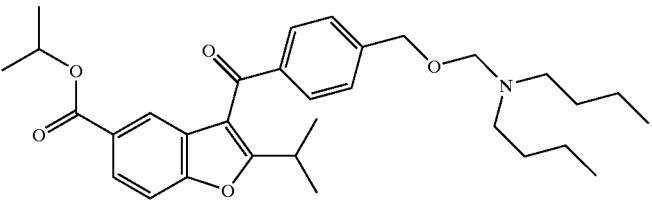 | Oxalate<br>White solid<br>M.p.: 106–108° C. | 95 |
| 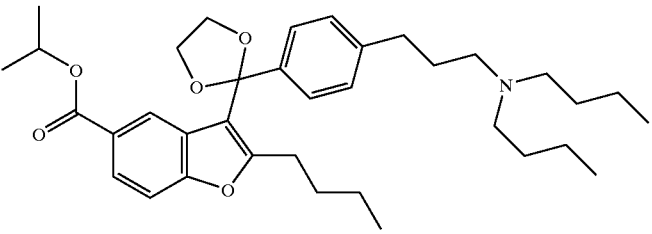 | Oxalate<br>Solid<br>M.p.: 106–108° C. | 96 |

| Compound | Characteristics | Example |
|---|---|---|
| [structure] | Oxalate<br>Amorphous solid | 97 |
| [structure] | Oxalate<br>Solid<br>M.p.: 87–89° C. | 98 |
| [structure] | Oxalate<br>White solid<br>M.p.: 133–135° C. | 99 |

¹H N.M.R. Spectra at 200 MHz

Example 25

Solvent: DMSO at 2.5 ppm
DOH at 3.3 ppm
δ (ppm): 0.8; triplet; 3H, 1CH₃
1 to 1.4; triplet + doublet; 12H, 4CH₃
1.6; quintet; 2H, 1CH₂
2; multiplet; 2H, 1CH₂
2.8; multiplet; 4H, CH₂ phenyl, CH₂—CH=
3.1; multiplet; 6H; 3NCH₂
5.1; multiplet; 1H, O—CH
7.4; doublet; 2H, 2 aromatic H
7.8; doublet; 3H, 3 aromatic H
8.0; double doublet; 1H, 1 aromatic H
8.1; doublet; 1H, 1 aromatic H Example 32

Solvent: DMSO at 2.5 ppm
DOH at 3.3 ppm
δ (ppm): 0.7; triplet + doublet; 9H, 3CH₃
1; multiplet; 2H, 1CH₂
1.1; doublet; 6H, 2CH₃
1.4 to 2; unresolved peak; 9H, 4CH₂, 1CH
2.4 to 3.4; unresolved peak; 10H, 3NCH₂, 1 phenyl CH₂, 1CH₂—CH=
5; 1 septet; 1H, 10CH
7.4; doublet; 2H, 2 aromatic H
7.7; multiplet; 3H, 3 aromatic H
7.9; double doublet; 1H, 1 aromatic H
8; doublet; 1H, 1 aromatic H Example 33

Solvent: DMSO at 2.5 ppm
δ (ppm): 0.85; triplet; 3H, CH₃
1 to 2.25; unresolved peak; 25H, 3CH₃, 8CH₂
2.85; multiplet; 4H, 2 phenyl CH₂
3 to 3.45; unresolved peak; 5H, NCH, 2NCH₂
5.15; septet; 1H, OCH
7.4 to 8.2; unresolved peak; 7H, 7 aromatic H
very broad signal centred at 7.5; 2COOH + DOH Example 42

Solvent: DMSO at 2.5 ppm
DOH at 3.3 ppm
δ (ppm): 0.8 to 1; triplet; 9H, 3CH₃
1 to 1.8; multiplet; 12, 6CH₂
2; multiplet; 2H, 1CH₃
2.7; multiplet; 4H, 1 phenyl CH₂, 1CH₂—CH=
3; multiplet; 6H, 3NCH₂
4.2; quartet; 2H, 10CH₂
7.4; doublet; 2H, 2 aromatic H
7.7; doublet; 3H, 3 aromatic H
7.9; double doublet; 1H, 1 aromatic H
8; doublet; 1H, 1 aromatic H Example 45

Solvent: DMSO at 2.5 ppm
δ (ppm): 0.6 to 1.7; unresolved peak; 27H, 5CH₃, 6CH₂
1.9; multiplet; 2H, CH₂
2.6 to 2.8; unresolved peak; 4H, 2CH₂
2.8 to 3.5; unresolved peak; 10H, 5NCH₂

-continued

| | |
|---|---|
| | 6.8; very broad signal; 2COOH, DOH |
| | 7.1 to 7.8; unresolved peak; 7H, aromatic ¹H |
| Example 46 | |
| Solvent: | DMSO at 2.5 ppm |
| δ (ppm): | 0.8; triplet; 3H, CH₃ |
| | 0.9; triplet; 6H, 2CH₃ |
| | 1 to 1.8; unresolved peak; 18H, 2CH₃, 6CH₂ |
| | 1.95; multiplet; 2H, CH₂ |
| | 2.75; triplet; 4H, 2CH₂ |
| | 3; multiplet; 6H; 3NCH₂ |
| | 5.9; very broad signal; 2COOH + DOH |
| | 7.3 to 8.1; unresolved peak; 7H, aromatic ¹H |
| | 8.3; doublet; 1H, NH |
| Example 58 | |
| Solvent: | DMSO |
| δ (ppm) | 0.8 (triplet, 3H); 0.9 (triplet, 6H); 1.1 to 2.2 (unresolved peak, 14H); 2.6 to 2.9 (unresolved peak, 4H); 2.9 to 3.2 (unresolved peak, 6H); 7.2 to 8.2 (unresolved peak; 7H) |
| Example 81 | |
| Solvent: | DMSO |
| δ (ppm) | 0.8 (triplet, 3H); 1.1 to 2.0 (unresolved peak, 6H); 2.6 (triplet,2H); 2.9 (triplet, 6H); 5.2 (septet, 1H); 7.1 to 8.1 (unresolved peak, 12H) |
| Example 92 | |
| Solvent: | DMSO |
| δ (ppm) | 0.3 to 2.0 (unresolved peak, 28H); 2.6 to 3.4 (unresolved peak, 13H); 3.7 (broad triplet, 2H); 4.6 (singlet, 2H); 7.0 to 7.9 (unresolved peak, 7H) |

EXAMPLE 47

A capsule was prepared according to known pharmaceutical techniques comprising the following ingredients:

| Ingredient | mg |
|---|---|
| Compound of the invention | 100.0 |
| Starch | 99.5 |
| Colloidal silica | 0.5 |

What is claimed is:

1. Benzofuran derivatives of general formula:

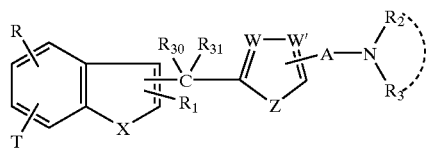 (1)

and their pharmaceutically acceptable salts, in which formula:

A represents a linear or branched $C_1$–$C_5$ alkylene group optionally substituted by a hydroxyl group or A represents a group of general formula:

$$—R_{19}—O—R_{20}— \quad (h)$$

in which $R_{19}$ and $R_{20}$, which are identical or different, each represent a linear or branched $C_1$–$C_4$ alkylene group, $R_{30}$ and $R_{31}$, taken together, represent a carbonyl group with the carbon to which they are attached or represent a group of general formula:

$$—O—R_{29}—O— \quad (m)$$

in which $R_{29}$ represents a $C_1$–$C_4$ alkylene group,

T represents hydrogen or a $C_1$–$C_4$ alkyl radical,

R represents:
the cyano, hydroxymethyl, formyl or tetrazolyl group, or
an ester group of general formula:

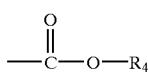 (a)

in which $R_4$ represents a linear or branched $C_1$–$C_6$ alkyl group or a $C_3$–$C_6$ cycloalkyl group, $R_1$ represents hydrogen, a linear or branched $C_1$–$C_6$ alkyl group, a $C_3$–$C_6$ cycloalkyl group, a benzyl group or a phenyl group optionally substituted by one or more substituents selected from halogen atoms, $C_1$–$C_4$ alkyl groups or $C_1$–$C_4$ alkoxy groups or $R_1$ represents a group of general formula:

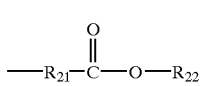 (i)

in which $R_{21}$ represents a linear or branched $C_1$–$C_4$ alkylene group and $R_{22}$ represents a linear or branched $C_1$–$C_4$ alkyl group or $R_1$ represents a group of general formula:

$$—R_{23}—OH \quad (j)$$

in which $R_{23}$ represents a linear or branched $C_1$–$C_6$ alkylene group, $R_2$ and $R_3$, which are identical or different, represent hydrogen, a linear or branched $C_1$–$C_6$ alkyl group optionally substituted by one or more halogen atoms or by a pyrrolidinyl group, a $C_3$–$C_6$ cycloalkyl group or a group of general formula:

$$—R_{24}—O—R_{25} \quad (k)$$

in which $R_{24}$ represents a linear or branched $C_1$–$C_4$ alkylene group and $R_{25}$ represents a linear or branched $C_1$–$C_4$ alkyl group, or $R_2$ and $R_3$, when they are taken together, represent a linear or branched $C_3$–$C_{10}$ alkylene group W, W' and Z are such that:
when W and W', which are identical, represent CH, Z represents —O— or —S—,
when W represents CH and W' represents C—$R_{13}$, Z represents

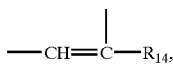

$R_{13}$ and
$R_{14}$ being identical or different and representing hydrogen, a halogen atom, a $C_1$–$C_4$ alkyl radical or a $C_1$–$C_4$ alkoxy radical, X represents —O—, these benzofuran derivatives being in the form of individual isomers or of mixtures of the latter.

2. Benzofuran derivatives according to claim 1 wherein A represents a linear or branched $C_1$–$C_5$ alkylene group.

3. Benzofuran derivatives according to claim 1 wherein $R_1$ represents hydrogen, a linear or branched $C_1$–$C_6$ alkyl group, a $C_3$–$C_6$ cycloalkyl group, a benzyl group or a phenyl group optionally substituted by one or more substituents selected from halogen atoms, $C_1$–$C_4$ alkyl groups or $C_1$–$C_4$ alkoxy groups.

4. Benzofuran derivatives according to claim 1 of general formula:

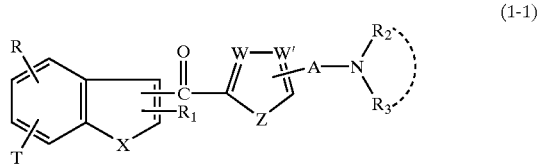

(1-1)

and their pharmaceutically acceptable salts, in which:

A represents a linear or branched $C_1$–$C_5$ alkylene group,

T represents hydrogen or a $C_1$–$C_4$ alkyl radical,

R represents:
the cyano, hydroxymethyl, formyl or tetrazolyl group, or
an ester group of general formula:ps

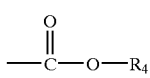

(a)

in which $R_4$ represents a $C_1$–$C_6$ alkyl or $C_3$–$C_6$ cycloalkyl group, $R_1$ represents hydrogen, a linear or branched $C_1$–$C_6$ alkyl group, a $C_3$–$C_6$ cycloalkyl group, a benzyl group or a phenyl group optionally substituted by one or more substituents selected from halogen atoms, $C_1$–$C_4$ alkyl groups or $C_1$–$C_4$ alkoxy groups, $R_2$ and $R_3$, which are identical or different, represent hydrogen, a linear or branched $C_1$–$C_6$ alkyl group or a $C_3$–$C_6$ cycloalkyl group, or $R_2$ and $R_3$, when they are taken together, represent a linear or branched $C_3$–$C_{10}$ alkylene group, W, W' and Z are such that:
when W and W', which are identical, represent CH, Z represents —O— or —S—,
when W represents CH and W' represents C—$R_{13}$, Z represents

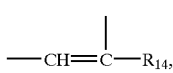

$R_{13}$ and $R_{14}$
being identical or different and representing hydrogen, a halogen atom, a $C_1$–$C_4$ alkyl radical or a $C_1$–$C_4$ alkoxy radical, X represents —O— these benzofuran derivatives being in the form of individual isomers or of mixtures of the latter.

5. Benzofuran derivatives according to claim 1 wherein R represents the isopropoxycarbonyl group.

6. Benzofuran derivatives according to claim 1 wherein $R_1$ and/or $R_2$ and/or $R_3$ represent the n-butyl group.

7. Benzofuran derivatives according to claim 1 in which:

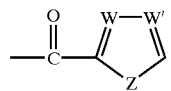

represents the benzoyl group.

8. Benzofuran derivatives according to claim 1 in which:

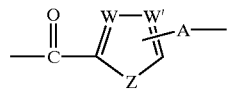

represents the benzoyl group substituted in the 4-position by an -A- group.

9. Benzofuran derivatives according to claim 1 wherein $R_1$ represents the n-butyl group, A represents the propylene group and $R_2$ and $R_3$, which are identical, represent the n-butyl group.

10. Isopropyl 2-butyl-3-[4-[3-(dibutylamino)propyl] benzoyl]-1-benzofuran-5- carboxylate and its pharmaceutically acceptable salts.

11. Isopropyl 2-butyl-6-methyl-3-[4-[3-(dibutylamino) propyl]benzoyl]-1-benzofuran-5-carboxylate and its pharmaceutically acceptable salts.

12. Benzofuran derivatives according to claim 1 in which the pharmaceutically acceptable salt is chosen maleate, fumarate, methanesulphonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate, p-toluenesulphonate and theophyllineacetate salts and the salts formed from an amino acid.

13. Isopropyl 2-butyl-3-[4-[3-(dibutylamino)propyl] benzoyl]-1-benzofuran-5-carboxylate fumarate.

14. Benzofuran derivatives according to claim 1 in which the pharmaceutically acceptable salt is chosen from the hydrochloride, hydrobromide, sulphate, sulphamate, phosphate and nitrate salts.

15. Isopropyl 2-butyl-3-[4-[3-(dibutylamino)propyl] benzoyl]-1-benzofuran-5-carboxylate sulphate.

16. Benzofuran derivatives according to claim 4 wherein R represents the isopropoxycarbonyl group.

17. Benzofuran derivatives according to claim 4 wherein $R_1$ and/or $R_2$ and/or $R_3$ represent the n-butyl group.

18. Benzofuran derivatives according to claim 4 in which:

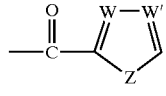

represents the benzoyl group.

19. Benzofuran derivatives according to claim 4 in which:

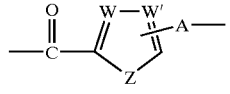

represents the benzoyl group substituted in the 4-position by an -A- group.

20. Benzofuran derivatives according to claim 4 wherein $R_1$ represents the n-butyl group, A represents the propylene group and $R_2$ and $R_3$, which are identical, represent the n-butyl group.

21. Benzofuran derivatives according to claim 4 in which the pharmaceutically acceptable salt is chosen from maleate, fumarate, methanesulphonate, benzoate, ascorbate, pamoate, succinate, hexamate, bismethylenesalicylate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate, p-toluenesulphonate and theophyllineacetate salts and the salts formed from an amino acid.

22. Benzofuran derivatives according to claim 4 in which the pharmaceutically acceptable salt is chosen from the hydrochloride, hydrobromide, sulphate, sulphamate, phosphate and nitrate salts.

23. Benzofuran derivatives according to claim 13 wherein the salt formed from an amino acid is a lysine or histidine salt.

* * * * *